(12) United States Patent
Mitrani

(10) Patent No.: US 6,372,482 B1
(45) Date of Patent: Apr. 16, 2002

(54) DEVICE AND METHOD FOR PERFORMING A BIOLOGICAL MODIFICATION OF A FLUID

(75) Inventor: Eduardo N. Mitrani, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/341,630

(22) PCT Filed: Jan. 9, 1998

(86) PCT No.: PCT/US98/00594

§ 371 Date: Jul. 15, 1999

§ 102(e) Date: Jul. 15, 1999

(87) PCT Pub. No.: WO99/49807

PCT Pub. Date: Oct. 7, 1999

Related U.S. Application Data

(63) Continuation of application No. 08/783,903, filed on Jan. 16, 1997, now abandoned.

(51) Int. Cl.$^7$ ................................................. A01N 1/02
(52) U.S. Cl. .................... 435/284.1; 435/1.1; 435/347; 435/373; 435/374; 210/601; 210/602
(58) Field of Search ........................ 435/1.1, 347, 373, 435/374, 284.1; 210/602, 601

(56) References Cited

U.S. PATENT DOCUMENTS

| | | | | |
|---|---|---|---|---|
| 3,734,851 A | * | 5/1973 | Matsumura | 210/22 |
| 5,773,285 A | * | 6/1998 | Park | 435/286.5 |
| 5,888,720 A | * | 5/1999 | Mitrani | 435/1.1 |

OTHER PUBLICATIONS

Parrish et al, Life Sciences 57(21):1887–1901, 1995.*

* cited by examiner

*Primary Examiner*—Francisco Prats

(57) ABSTRACT

A device for performing a biological modification of a fluid, particularly in order to assist or replace the functioning of an organ which normally performs this modification, including a collection of liver micro-organ cultures. The device of the present invention is preferably directly connected to a subject for performing this modification.

65 Claims, 15 Drawing Sheets

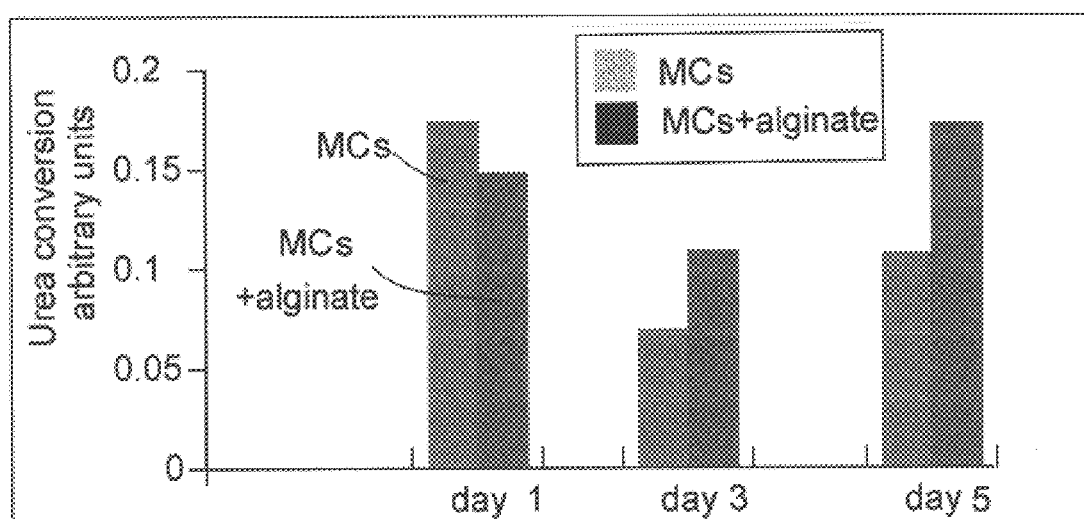
Fig. 13
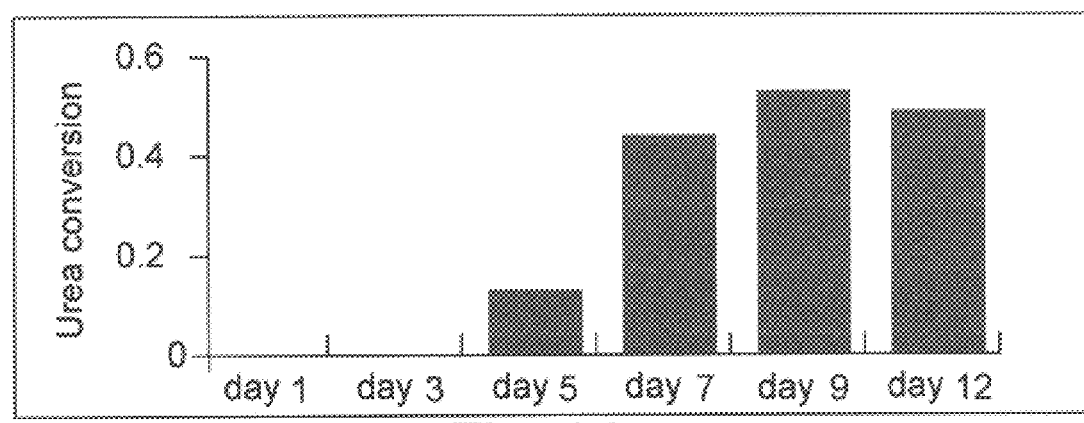
Fig. 14a
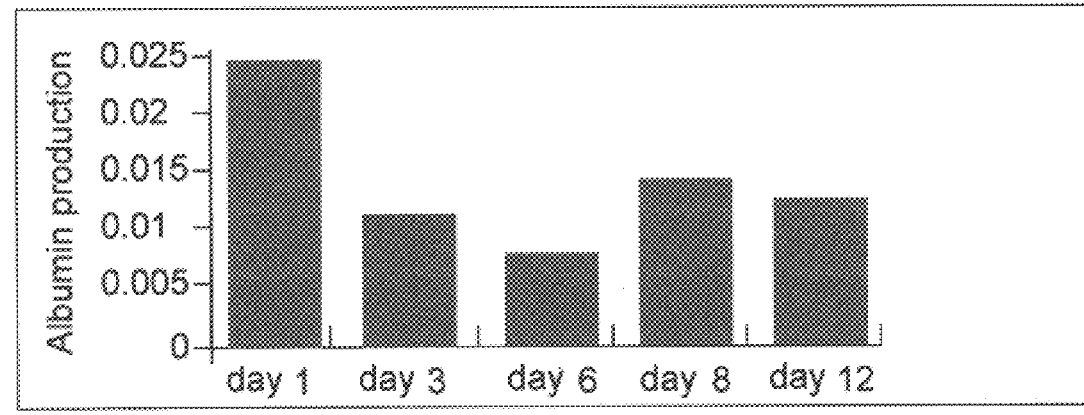
Fig. 14b Albumin

DEVICE AND METHOD FOR PERFORMING A BIOLOGICAL MODIFICATION OF A FLUID

This application is a National Stage Entry of PCT/US98/00594, filed Jan. 9, 1998, which is a continuation to U.S. Ser. No. 08/783,903, filed Jan. 16, 1997, now abandoned.

FIELD AND BACKGROUND OF THE INVENTION

The present invention relates to a device and a method for performing a biological modification of a fluid, and more particularly to a device and method for assisting or replacing an organ which normally performs such a modification of the fluid.

A number of organs in the body, such as the liver, modify fluids such as blood. The liver is a particularly complex organ because it acts both as a filter and as an active metabolic unit. As a filter, the liver removes toxic substances from the blood. In addition, the liver performs many biochemical functions such as detoxifying ammonia into urea, bilirubin metabolism, glycogen storage, lipid synthesis, drug metabolism, albumin secretion and clotting factor secretion. Thus, the liver has many important functions within the body which render it essential. If the liver should fail, the body would be unable to continue operating.

There are many causes of liver failure, including exposure to toxic substances, hepatitis, and genetic defects (Kasai, et. al. . *Artif. Organs*, 18:348–54, 1994). Currently, 70% of patients with acute liver failure die because of no available treatment (Kasai, et. al. . *Artif. Organs*, 18:348–54, 1994). Furthermore, 10–30% of patients die while awaiting donor liver organs (LePage, et al., *Am. J Crit. Care*, 3:224–7, 1994; Sussman, et al. *Artif. Organs*, 18:390–6, 1994; and Uchino & Matsushita, *Asaio J.*, 40:74–7, 1994).

A bedside life-support device that could temporarily perform liver function during liver failure is called an Extracorporeal Liver Assist Device (ELAD). The development and commercialization of such a device would clearly be of enormous benefit for a number of reasons (Fox et al, *Am. J. Gastroenterol.*, 88:1876–81, 1993). An ELAD would benefit the roughly 2,000 patients with fulminant liver failure (FH) in the U.S. each year (Hoofnagle, et al., *Hepatology*, 21:240–52, 1995). It could also be used as a bridge to liver transplantation for patients awaiting donor organs.

An ELAD that would function for several weeks could in addition allow for recovery to normal functioning of the patient's own liver. Since it is unlikely that every hepatocyte is destroyed in a damaged liver, adequate liver support for two to three weeks could allow surviving hepatocytes to repopulate the damaged liver. Fewer than a dozen hepatocytes are required to repopulate the liver in an animal model of lethal hepatic disease (Sandgren et al., *Cell*, 66:245–56, 1991). A patient with 90–95% liver necrosis should be able to recover sufficient function to survive independently after only a few days of support (Sussman et al. *Artif. Organs*, 18:390–6, 1994).

In an attempt to provide such an ELAD, several purely mechanical, non-biological blood-treatment devices have been developed. In the most basic form, the purpose of these devices is to selectively remove toxins and add nutrients across a membrane with a relatively small pore size. One of the most advanced of these non-biological devices has been developed by Hemocleanse™ and has recently received FDA approval. In a randomized, controlled clinical trial using the Hemocleanse™ apparatus, removal of metabolites was limited and there was no significant effect on blood ammonia levels (Hughes et al., *Int. J. Artif. Org.*, 17:657–662, 1994). Clearly, liver function is extremely complex and is unlikely to be replaced by a solely mechanical or a chemical device at this time.

Other currently available ELADs use biological materials as a starting point. For example, one of the most clinically tested ELADs uses a transformed immortalized human cell line as a source for hepatocyte-like cells (Sussman, et al., *Artif. Organs*, 18:390–6, 1994). Initial trials of this device were performed under "Emergency Use of Unapproved Medical Devices", or "Investigational Device Exemption". Efficacy was not determined, but no serious adverse side effects were observed except for clotting that was managed by drug treatment. While the use of an immortalized human cell line is convenient because it provides an expendable source of cells, there are two major reasons why it may not be ideal. Firstly, there are obvious safety and regulatory concerns about using immortalized cell lines in clinical practice. Secondly, immortalized cells would not be expected to retain all the normal physiological characteristics of primary hepatocytes, particularly after industrial scale expansion (Sussman et. al., *Artif Organs*, 18:390–6, 1994).

A second general approach for obtaining liver cells as a source for an ELAD, is the isolation of liver cells or tissue from intact livers. In previous attempts, cells from livers have usually been disassociated using enzymes such as collagenase, which disrupts the normal micro architecture of the liver. Some attempts have been used to use liver pieces, but the shape of these pieces have not been designed for proper surface area to volume ratios necessary for optimal tissue maintenance (Lie et al., *Res Exp Med* (*Berl*) 185:483–94, 1985)

One current limitation is the ability of current methods of culturing mammalian liver cells to provide conditions which allow cells to assemble into tissues which simulate the spatial three-dimensional form of actual tissues in the intact organism. Conventional tissue culture processes limit, for similar reasons, the capacity for cultured tissues to express a highly functionally specialized or differentiated state considered crucial for mammalian cell differentiation and secretion of specialized biologically active molecules of research and pharmaceutical interest. Unlike microorganisms, the cells of higher organisms such as mammals form themselves into high order multicellular tissues. Although the exact mechanisms of this self-assembly are not known, in the cases that have been studied thus far, development of cells into tissues has been found to be dependent on orientation of the cells with respect to each other or another anchorage substrate and/or the presence or absence of certain substances such as hormones. In summary, no conventional culture process used in the organ assist devices to date is capable of simultaneously achieving proper functioning of the cells in vitro while at the same time maintaining critical cell/cell/substrate interactions and proper microenvironment to allow excellent modeling of in vivo organ tissue structure and function.

In the liver, the unique juxtaposition of diverse cell populations and matrix components in harmony with the angio architecture results in a delicate bioecological system. It is therefore unlikely that standard cell cultures of hepatocytes will perform even the minimal liver functions. As mentioned previously, the cells of higher organisms such as mammals form themselves into high order multicellular tissues. An example of physical contact between a cell and a noncellular substrate (matrix) is the physical contact between an epithelial cell and its basal lamina. Examples of functional contact between one cell and another cell includes electrical or chemical communication between cells. For example, cardiomyocytes communicate with other cardiomyocytes via electrical impulses. In addition, many cells communicate with other cells via chemical messages, e.g., hormones, which either diffuse locally (paracrine signaling and autocrine signaling), or are transported by the vascular system to more remote locations (endocrine signaling). Examples of paracrine signaling between cells are the messages produced by various cells (known as enteroendocrine cells) of the digestive tract, e.g., pyloric D cells which secrete somatostatin which in turn inhibits the release of gastrin by nearby pyloric gastrin (G) cells.

This microarchitecture can be extremely important for the maintenance of a tissue explant of an organ in minimal media, e.g., without exogenous sources of serum or growth factors, because the liver tissue can be sustained in such minimal media by paracrine and autocrine factors resulting from specific cellular interactions within the micro-organ, The preparation of such a micro-organ culture is described in U.S. patent application Ser. No. 08/482,364, herein incorporated by reference. In the preparation of a micro-organ culture, the populations of cells which make up the explant are isolated from a liver in a manner that preserves the natural affinity of one cell to another, e.g., to preserve layers of different cells as present in the organ itself For example, in skin micro-organ cultures, keratinocytes of the epidermis remain associated with the stroma and the normal tissue architecture is preserved including the hair follicles and glands. This basic structure is common to all organs, for instance, which contain an epithelial component. Moreover, such an association facilitates intercellular communication. This is particularly important in differentiating cells where induction is defined as the interaction between one (inducing) and another (responding) tissue or cell, as a result of which the responding cells undergo a change in the direction of differentiation. Moreover, inductive interactions occur in embryonic and adult cells and can act to establish and maintain morphogenetic patterns as well as induce differentiation (Gurdon, *Cell*, 68:185–199, 1992).

Furthermore, the micro-organ cultures prepared according to U.S. patent application Ser. No. 08/482,364 preserve normal liver tissue architecture even when cultured for prolonged periods of time. Because these cultures can be maintained in controlled and uniform conditions and yet closely resemble tissue in vivo, they provide a unique continuous source of functional liver cells in vitro.

Unfortunately, none of the prior art organ assist devices, or related devices in the prior art, uses micro-organ cultures to perform a biological modification of a fluid.

Therefore, there is a decided need in the art for a device and a method for performing a biological modification of a fluid, particularly for assisting or replacing a failed organ of a subject, which can perform the functions of the organ and which includes a micro-organ culture.

SUMMARY OF THE INVENTION

According to the present invention there is provided a device for performing a biological modification of a fluid, the device comprising: (a) a chamber having an inlet for intake of the fluid and an outlet for outflow of the fluid, and (b) a collection of micro-organ cultures of an organ for performing the biological modification of the fluid, each individual micro-organ culture of the collection including cells and having dimensions, such that cells positioned deepest within the individual micro-organ culture are at least about 150 micrometers and not more than about 225 micrometers away from a nearest surface of the individual micro-organ culture, thereby in vivo organ architecture (organ structure) of organ units (e.g., acinus units of liver) is maintained within each individual micro-organ culture, the collection of micro-organ cultures being located within the chamber and the collection of micro-organ cultures being in contact with at least a portion of the fluid flowing through the chamber.

As used herein, the term "MC" refers to micro-organ culture.

Preferably, the organ is liver. Also preferably, the collection of micro-organ cultures includes cells from the organ, such that intercellular contacts between the cells are preserved. Most preferably, each of the collection of micro-organ cultures is characterized by an Aleph of at least about 2.6 mm$^{-1}$.

According to preferred embodiments of the present invention, the micro-organ culture is substantially encapsulated by a sheet of a biocompatible polymer, the sheet being located substantially within the chamber. Preferably, the sheet has a first dimension in a range of from about 30 cm to about 90 cm, a second dimension in a range of from about 30 cm to about 80 cm and a third dimension in a range of from about 300 micrometers to about 900 micrometers. Also preferably, a plurality of the sheets are incorporated substantially parallel in orientation within the chamber, such that fluid flows freely between the sheets.

According to another embodiment of the present invention, there is provided a device for performing a biological modification of a fluid of a subject, including: (a) a chamber having an inlet for intake of the fluid and an outlet for outflow of the fluid; (b) a collection of micro-organ cultures for performing the biological modification of the fluid, each individual micro-organ culture of the collection including cells and having dimensions, such that cells positioned deepest within the individual micro-organ culture are at least about 150 micrometers and not more than about 225 micrometers away from a nearest surface of the individual micro-organ culture, thereby in vivo organ architecture of organ units is maintained within each individual micro-organ culture, the collection of micro-organ cultures being located within the chamber and the collection of micro-organ cultures being in contact with at least a portion of the fluid flowing through the chamber; (c) a first tube having first and second ends, the first end for coupling to the subject for receiving the fluid from the subject, the second end for coupling to the inlet; and (d) a second tube having first and second ends, the first end for coupling to the outlet and the second end for coupling to the subject to return the fluid to the subject after the biological modification.

According to still further embodiments of the present invention, there is provided a method of performing a biological modification of a fluid from a subject, the method comprising the step of perfusing a chamber containing a collection of micro-organ cultures with the fluid from the subject, such that the collection of micro-organ cultures performs the biological modification on the fluid, wherein each individual micro-organ culture of the collection includes cells and has dimensions, such that cells positioned deepest within the individual micro-organ culture are at least about 150 micrometers and not more than about 225 micrometers away firm a nearest surface of the individual micro-organ culture, thereby in vivo organ architecture of organ units is maintained within each individual micro-organ culture.

According to still further embodiments of the present invention, there is provided a method of preparing a continuous planar organ. The method comprising the steps of (a) obtaining a collection of individual micro-organ cultures of an organ, such that each of the individual micro-organ culture of the collection includes cells and has dimensions, such that cells positioned deepest within the individual micro-organ culture are at least about 150 micrometers and not more than about 225 micrometers away from a nearest surface of the individual micro-organ culture, thereby in vivo organ architecture of organ units is maintained within each individual micro-organ culture; and (b) adding (e.g., layering) a suspension of cells from the organ onto the micro-organ cultures and coculturing the suspension of cells in presence of the collection of micro-organ cultures, such that the continuous planar organ is formed from an admixture of cells derived from the micro-organ cultures and the cells in suspension.

According to a preferred embodiment of the present invention, the collection of liver micro-organ cultures is provided within a continuous liver planar organ formed by culturing hepatocyte cells in presence of the collection of liver micro-organ cultures, such that the continuous liver planar organ is formed from an admixture of cells derived from the micro-organ cultures and the hepatocyte cells.

According to still further embodiments of the present invention, there is provided a method of preparing a continuous liver planar organ. The method comprising the steps of (a) obtaining a collection of individual liver micro-organ cultures, such that each of the individual micro-organ culture of the collection includes liver cells and has dimensions, such that cells positioned deepest within the individual micro-organ culture are at least about 150 micrometers and not more than about 225 micrometers away from a nearest surface of the individual micro-organ culture, thereby in vivo liver architecture of acinus units is maintained within each individual micro-organ culture; and (b) adding (e.g., layering) a suspension of hepatocyte cells onto the micro-organ cultures and coculturing the suspension of cells in presence of the collection of liver micro-organ cultures, such that the continuous planar liver organ is formed from an admixture of cells derived from the micro-organ cultures and the hepatocyte cells.

Additional features of the invention are described hereinunder.

BRIEF DESCRIPTION OF THE DRAWINGS

The invention herein described, by way of example only, with reference to the accompanying drawings, wherein:

FIG. 13 shows that mouse liver micro-organ cultures remain functional when cultured in 100% fetal calf serum;

FIGS. 14A and 14B show that rat liver micro-organ cultures are metabolically active when encapsulated in alginate sheets, frozen and then thawed;

DESCRIPTION OF THE PREFERRED EMBODIMENTS

Figure 1A:
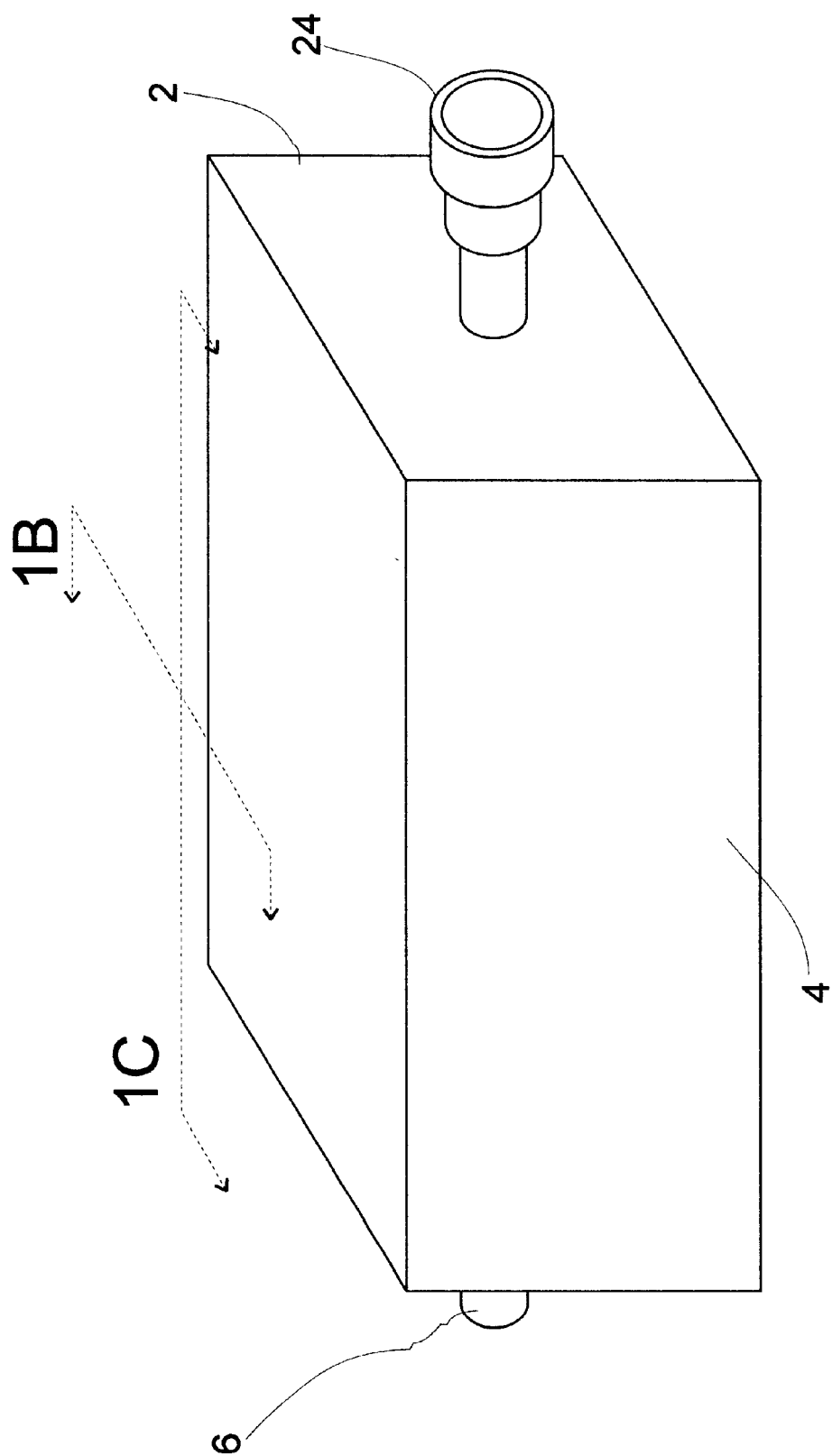
FIGS. 1A–1D are diagrammatic sketches of an exemplary bioreactor for housing metabolically active micro-organ cultures.

The present invention is of a device for performing a biological modification of a fluid, particularly in order to assist or replace the functioning of an organ which normally performs this modification. As used herein, the phrase "biological modification of a fluid" refers to a change in the fluid's biological constituents which are regularly introduced into, removed from or modified within the fluid by secretion, uptake or as a result of a catalytic activity exerted by the organ which normally performs this modification in vivo in blood. The device of the present invention is preferably directly connected to a subject for performing this modification of the fluid of the subject. As used herein, the term "subject" refers to a human or lower animal to whom the device of the present invention is connected, or on whom the method of the present invention is practiced.

The device of the present invention includes a micro-organ culture derived from the tissue for which augmented functioning, is desired. The fluid to be biologically modified, such as whole blood or plasma, enters the device of the present invention and is in communication with the micro-organ culture. The micro-organ culture then biologically modifies the fluid. For example, detoxification and other hepatic biological activities can be augmented using liver micro-organ cultures.

Moreover, it will be apparent that other organ functions can be enhanced depending on the source of the tissue for the micro-organ culture. For example, paracrine functions can be enhanced using pancreatic micro-organ cultures for insulin or glucagon production. Likewise, anterior lobe pituitary gland micro-organ cultures can be used to augment production of hormones which regulate the proper functioning of the thyroids, gonads, adrenal cortex, and other endocrine organs, and posterior lobe pituitary gland micro-organ cultures can be used to augment production of hormones having antidiuretic and oxytocic action.

As described in further detail below, a salient feature of the use of these micro-organ cultures is the preservation of the cellular micro-architecture of the original organ. The device of the present invention is based, in part, upon the discovery that under defined circumstances growth of cells in different tissue layers of an organ explant, e.g., mesenchymal and epithelial layers, can be activated to proliferate, differentiate and function in culture. As used herein, the term "explant" refers to tissue removed from an organ.

Moreover, the cell-cell and cell-matrix interactions provided in the explant itself are sufficient to support cellular homeostasis, thereby sustaining the microarchitecture and function of the organ for prolonged periods of time. As used herein, the term "homeostasis" is defined as an equilibrium between cell proliferation and cell loss.

The support of cellular homeostasis preserves, for example, the natural cell-cell and cell-matrix interactions occurring in the source organ. Thus, orientation of the cells with respect to each other or to another anchorage substrate, as well as the presence or absence of regulatory substances such as hormones, permits the appropriate maintenance of biochemical and biological activity of the source organ. Moreover, the micro-organ cultures can be maintained in culture without significant necrosis for relatively long periods of time, preferably at least about twenty four hours, though cultures of at least 48 days or longer will be typical.

Although the device of the present invention can be used to assist or replace the functioning of any organ which biologically modifies a fluid, the following discussion focuses on the liver purely for illustrative purposes.

Source of explants for the micro-organ culture

Examples of animals from which the liver micro-organ cultures can be isolated for use in the device of the present invention include humans and other primates, swine, such as wholly or partially inbred swine (e.g., miniature swine, and transgenic swine), rodents, etc. In a preferred embodiment, the source of the liver tissue could be allogeneic liver tissue, such as a small lobe of the human liver which is unsuitable for transplantation but still contain viable hepatocytes.

In another preferred embodiment, a more reliable source would be a xenogenic source including, but not limited to, a cow, goat or preferably a pig liver. Although long term exposure to xenogenic antigens would cause immunological reactions, in the short term, the immune response has not been a problem in initial clinical experience, because the subject's blood cells are prevented from coming into contact with the liver micro-organ cultures.

The growth media

There are a large number of tissue culture media that exist for culturing cells from animals. Some of these are complex and some are simple. While it is expected that liver micro-organ cultures may grow in complex media, it has been shown in U.S. patent application Ser. No. 08/482,364 that the cultures can be maintained in a simple medium such as Dulbecco's Minimal Essential Media. Furthermore, although the cultures may be grown in a media containing sera or other biological extracts such as pituitary extract, it has been shown in U.S. patent application Ser. No. 08/482, 364 that neither sera nor any other biological extract is required. Moreover, the organ cultures can be maintained in the absence of sera for extended periods of time. In preferred embodiments of the invention, growth factors are not included in the media during maintenance of the cultures in vitro.

The point regarding growth in minimal media is important. At the present, most media or systems for prolonged growth of mammalian cells incorporate undefined proteins or use feeder cells to provide proteins necessary to sustain such growth. Because the presence of such undefined proteins can interfere with the intended end use of the subject liver micro-organ cultures, it will generally be desirable to culture the explants under conditions to minimize the presence of undefined proteins.

As used herein the language "minimal medium" refers to a chemically defined medium which includes only the nutrients that are required by the cells to survive and proliferate in culture. Typically, minimal medium is free of biological extracts, e.g., growth factors, serum, pituitary extract, or other substances which are not necessary to support the survival and proliferation of a cell population in culture. For example, minimal medium generally includes at least one amino acid, at least one vitamin, at least one salt, at least one antibiotic, at least one indicator, e.g., phenol red, used to determine hydrogen ion concentration, glucose, and at least one antibiotic, and other miscellaneous components necessary for the survival and proliferation of the cells. Minimal medium is serum-free. A variety of minimal media are commercially available from Gibco BRL, Gaithersburg, Md., as minimal essential media.

However, while growth factors and regulatory factors need not be added to the media, the addition of such factors, or the inoculation of other specialized cells may be used to enhance, alter or modulate proliferation and cell maturation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring negative growth factors, fibroblast growth factors, and members of the transforming growth factor-beta family.

Culture Vessel

The micro-organ cultures may be maintained in any suitable culture vessel and may be maintained at 37° C. in 5% $CO_2$. The cultures may be shaken for improved aeration.

With respect to the culture vessel in/on which the micro-organ cultures are preferably provided, it is noted that in a preferred embodiment such a vessel may generally be of any material and/or shape. A number of different materials may be used to form the vessel, including but not limited to: nylon (polyamides), dacron (polyesters), polystyrene, polypropylene, polyacrylates, polyvinyl compounds (e.g., polyvinylchloride), polycarbonate (PVC), polytetrafluoroethylene (PTFE; teflon), thermanox (TPX), nitrocellulose, cotton, polyglycolic acid (PGA), cat gut sutures, cellulose, gelatin, dextran, etc. Any of these materials may be woven into a mesh.

Where the cultures are to be maintained for long periods of time or cryopreserved, non-degradable materials such as nylon, dacron, polystyrene, polyacrylates, polyvinyls, teflons, cotton or the like may be preferred. A convenient nylon mesh which could be used in accordance with the invention is Nitex, a nylon filtration mesh having an average pore size of 210 mm and an average nylon fiber diameter of 90 mm (#3 -210/36, Tetko, Inc., N.Y.).

Dimensions of the Explant

In addition to isolating an explant which retains the cell-cell, cell-matrix and cell-stroma architecture of the originating tissue, the dimensions of the explant are important to the viability of the cells therein, e.g., where the micro-organ culture is intended to be sustained for prolonged periods of time, such as 7–21 days or longer.

Accordingly, the dimensions of the tissue explant are selected to provide diffusion of adequate nutrients and gases such as oxygen to every cell in the three dimensional micro-organ, as well as diffusion of cellular waste out of the explant so as to minimize cellular toxicity and concomitant death due to localization of the waste in the micro-organ. Accordingly, the size of the explant is determined by the requirement for a minimum level of accessibility to each cell in the absence specialized delivery structures or synthetic substrates.

It has been discovered, as described in U.S. patent application Ser. No. 08/482,364, that this accessibility can be maintained if the surface to volume index falls within a certain range.

This selected range of surface area to volume index provides the cells access to nutrients and to avenues of waste disposal by diffusion in a manner similar to cells in a monolayer. This level of accessibility can be attained and maintained if the surface area to volume index, defined herein as "Aleph or Aleph index" is at least about 2.6 mm$^{-1}$. The third dimension has been ignored in determining the surface area to volume index because variation in the third dimension causes ratiometric variation in both volume and surface area. However, when determining Aleph, a and x should be defined as the two smallest dimensions of the tissues slice.

However, when determining Aleph, a and x should be defined as the two smallest dimensions of the tissue slice.

As used herein, "Aleph" refers to a surface area to volume index given by a formula 1/x+1/a, wherein x=tissue thickness and a=width of tissue in mm. In preferred embodiments, the Aleph of an explant is in the range of from about 2.7 mm$^{-1}$ to about 25 mm$^{-1}$, more preferably in the range of from about 2.7 mm$^{-1}$ to about 15 mm$^{-1}$, and even more preferably in the range of from about 2.7 mm$^{-1}$ to about 10 mm$^{-1}$.

Examples of Aleph are provided in Table 1 wherein, for example, a tissue having a thickness (x) of 0.1 mm and a width (a) of 1 mm would have an Aleph index of 11 mm$^{-1}$.

TABLE 1

Different values for the surface area to volume ratio index "Aleph", as a function of a (width) and x (thickness) in mm$^{-1}$

| | Values of Aleph | | | | |
|---|---|---|---|---|---|
| x(mm) | a = 1 | a = 2 | a = 3 | a = 4 | a = 5 |
| 0.1 | 11 | 10.51 | 10.33 | 10.2 | 10.2 |
| 0.2 | 6 | 5.5 | 5.33 | 5.25 | 5.2 |
| 0.3 | 4.3 | 3.83 | 3.67 | 3.58 | 3.53 |
| 0.4 | 3.5 | 3 | 2.83 | 2.75 | 2.7 |
| 0.5 | 3 | 2.5 | 2.33 | 2.25 | 2.2 |
| 0.6 | 2.66 | 2.16 | 2 | 1.91 | 1.87 |
| 0.7 | 2.4 | 1.92 | 1.76 | 1.68 | 1.63 |
| 0.8 | 2.25 | 1.75 | 1.58 | 1.5 | 1.45 |
| 0.9 | 2.11 | 1.61 | 1.44 | 1.36 | 1.31 |
| 1.0 | 2 | 1.5 | 1.33 | 1.25 | 1.2 |
| 1.2 | 1.83 | 1.3 | 1.16 | 1.08 | 1.03 |
| 1.3 | 1.77 | 1.26 | 1.1 | 1.02 | 0.96 |
| 1.6 | 1.625 | 1.13 | 0.96 | 0.88 | 0.83 |
| 2.0 | 1.5 | 1 | 0.83 | 0.75 | 0.7 |

Thus, for example, cells positioned deepest within an individual micro-organ culture or explant are at least about 150 micrometers and not more than about 225 micrometers away from a nearest surface of the individual micro-organ culture, thereby in vivo architecture is preserved while at the same time it is ensured that no cell is farther than about 225 micrometers from the source of gases and nutrients.

For a century the basic structural and functional unit of the liver thought to be the lobule which is a polygonal unit, about 700 microns in diameter and 2 mm long. Since the fifties a smaller unit called the acinus has been recognized as the basic structural and functional unit in the liver. An acinus is a roughly ovoid mass of parenchymal cells arranged around a terminal artery, a venule and a bile duct that branch laterally from the portal area. At either end of the acinus present is a vessel known as the terminal hepatic venule (this vessel was referred to as the central vein in the old lobule terminology). The acinus is a small unit of about 300–450 microns at its smaller dimension, and it includes sectors of two neighbouring classical lobules. It should be pointed out that since its discovery the acinus is known to be the smallest structural and functional unit of the liver and it also establishes the maximum distance of any liver cell from a source of gases and nutrients. Thus, the micro architecture of the liver as exemplified by the acinus establishes that no cell within the liver is more than about 150–225 microns away from a source of nutrients. In fact this is true for any other body organ because, apparently, about 150–225 microns establishes the upper limit of effective diffusion of gases and nutrients. Additional descriptive data of acinus structure and function can be found in any histology text books. For example, in "A text book of histology". Bloom and Fawcett Eds. 12th Edition Chatman and Hall. N.Y.-London. 1994. Pages 652–656.

Without being bound by any particular theory, a number of factors provided by the three-dimensional culture system may contribute to its success.

First, the appropriate choice of the explant size, e.g., by use of the above Aleph calculations, provides appropriate surface area to volume ratio for adequate diffusion of nutrients to all cells of the explant, and adequate diffusion of cellular waste away from all cells in the explant.

Second, because of the three-dimensionality of the explant, various cells continue to actively grow, in contrast to cells in monolayer cultures, which grow to confluence, exhibit contact inhibition, and cease to grow and divide. The elaboration of growth and regulatory factors by replicating cells of the explant may be partially responsible for stimulating proliferation and regulating differentiation of cells in culture, e.g., even for the micro-organ culture which is static in terms of overall volume.

Third, the three-dimensional matrix of the explant retains a spatial distribution of cellular elements which closely approximates that found in the counterpart organ in vivo.

Fourth, the cell-cell and cell-matrix interactions may allow the establishment of localized micro-environments conducive to cellular maturation. It has been recognized that maintenance of a differentiated cellular phenotype requires not only growth/differentiation factors but also the appropriate cellular interactions. The present invention effectively mimics the tissue micro-environment.

Biological activity of liver micro-organ cultures

The liver micro-organ cultures included in the device of the present invention are believed capable of performing all classes of the "liver-specific" biological functions. Exemplary functions include the ability to perform ammonia and urea metabolism, and albumin production. These liver-specific biological functions are of particular importance where the cells are to be used in a liver assist device (LAD).

For support of subjects in the form of relatively short term LADS, such as subjects with fulminant hepatic failure (FHF), subjects awaiting liver transplantation, or subjects with nonfunctioning liver grafts, the liver-specific biological functions noted above are believed to be of central importance. However, notwithstanding the above, there may be others of equal or greater importance. The other functional deficits can be provided by other means (such as by provision of glucose and monitoring of glucose levels) or do not require acute attention (for example, conjugation of bile acids or bile pigment production, or drug metabolic activity).

The levels of liver-specific biological activity "sufficient to support" a subject suffering from hepatic failure or insufficiency are those which will result in normal or near normal levels of serum proteins, ammonia conversion to urea, coagulation factors, amino acids, and other metabolites produced in or metabolized by the liver.

These improvements may be measured biochemically or by an improvement in the subject's clinical status. These various molecules, metabolic and clinical parameters and products and the physiological as well as pathological ranges of their concentrations or levels are well known in the art and are set, forth, for example, in Zakim & Boyer, Hepatology; A Textbook of Liver Disease, W. B.Saunders Company; Harcourt, Brace, Jovanovich, Inc., Philadelphia, London, Toronto, Montreal, Sydney, Tokyo, (1990), which is hereby incorporated by reference.

Storage of the Micro-organ Culture

The micro-organ culture used as part of the present invention will preferably be prepared and cryopreserved by gradually freezing them for example in the presence of 10% DMSO (Dimethyl Sulfoxide) and 20% serum and storing them at −160° C. until required. In a preferred embodiment the liver micro-cultures will be encapsulated into sheets in an semi-permeable matrix such as alginate, as shown in FIG. 2B, and cryopreserved by gradually freezing them for example in the presence of standard culture medium such as Ham's F12 with 10% DMSO and 20% serum. The frozen sheets will then be stored at −160° C. As an example, the planar sheets containing the micro-organ cultures could be inserted into a sterile synthetic plastic bag sealed on all sides and of dimensions closely similar to those of the sheet. The bag would contain one plastic tubing input at one end and one plastic tubing output at the opposite end of the bag. The plastic bag containing the planar sheet with the micro-organ cultures could then be perfused with standard culture medium such as Ham's F12 with 10% DMSO and 20% serum and gradually frozen and stored at −160° C.

When required, the frozen sheets or the frozen micro-organ cultures will be thawed and assembled into the device of the present invention, preferably on site, and then connected to the system.

Use of micro-organ cultures to form continuous artificial planar organs

The present invention is based on the discovery that if the microarchitecture of an organ is maintained and conditions (e.g., its dimensions) are selected to ensure that all cells are within a reasonable distance from a source of gases and nutrients then the cells can function ex vivo similar to as they do it vivo.

The experiments described in the examples section below (see example 13) show behaviour of liver MC cultures as a function of thickness. Function was established by the capacity of the liver MC cultures to express a foreign gene when transduced into the cultures ex vivo. It is clearly shown that MCs of a thickness of 450 micrometers gave the best results. This data was corroborated by histological examination of the cultures.

Thus, the sheets of MCs according the present invention can be regarded as planar organs, each sheet essentially represents an organ that has been deconvoluted. When removed from the body, normal adult organs lack the system support and circulation necessary to provide adequate exchange of nutrients and gases to each cell in the organ. On the other hand, ex vivo planar organs as described herein, ensure (i) that the organ structure is preserved, although in a planar configuration, while at the same time (ii) no cell in the organ is more than about 150–225 micrometers away from the source of nutrients.

According to another embodiment of the present invention a continuous planar organ is prepared and used to implement the method and the device according to the present invention.

The continuous planar organ is prepared as follows. A collection of individual micro-organs prepared as described is used as a feeder or substrate layer to support or sustain cells which are derived from the same organ, yet were grown in suspension. The feeder layer therefore provides the cells is suspension with a surface onto which they adhere, proliferate and exert their biological functions. Cells derived from the adhered cells together with the collection of individual MCs, eventually produce a coherent and continuous sheet of a planar organ. For example, a continuous liver planar organ is prepared by coculturing a collection of individual liver micro-organ cultures and hepatocytes.

Thus, the continuous planar organ constitutes a reengineered coherent organ in which the basic organ microstructure or architecture is maintained. Due to its planar dimensions the continuous planar organ according to the present invention ensures that no cell is more than about 150–225 micrometers away from the source of nutrients, thereby obviating the need for circulation.

It will be appreciated that the concept of using a monolayer of cells as a feeder or substrate layer on which other cell types can be grown is not new and has been used extensively and successfully in the past.

However, the concept of using a collection of micro-organs as a feeder or substrate layer or rather as a "feeder organ" is new and presents several advantages, mainly the fact that the cells grown on the feeder organ are presented with highly complex substrate which is more similar to the substrate encountered by cells as they proliferate in vivo.

Figure 1B:
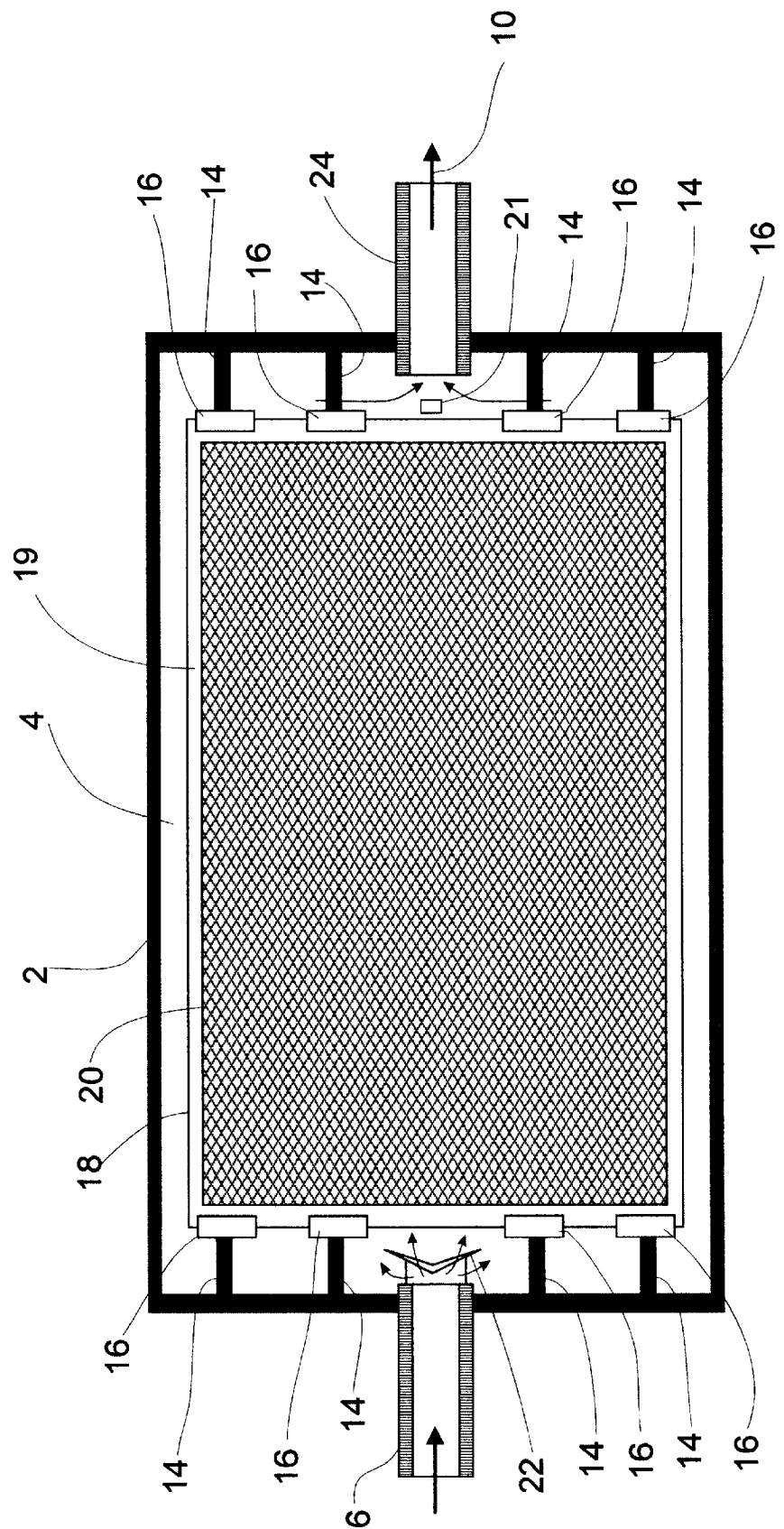
Figure 1C:
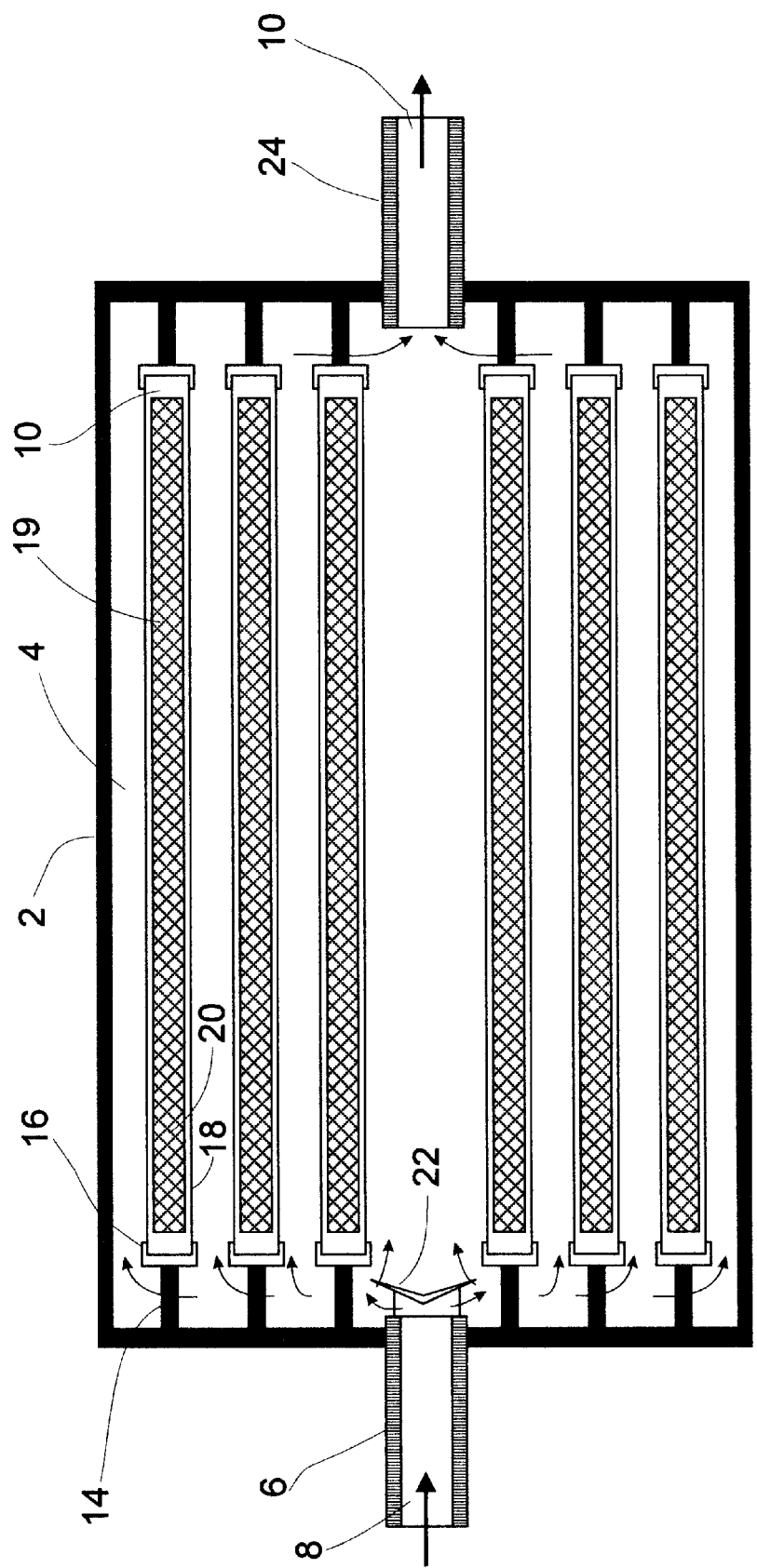

The device and method of the present invention may be better understood with reference to the examples, illustrations and drawings given below. Referring now to the drawings, FIGS. 1A–1C show a bioreactor suitable for use with the device of the present invention. A bioreactor 2 is a chamber 4 having a perfusion inlet 6 and a perfusion outlet 24 with a flow path for fluid defined therebetween. Fluid flows in through inlet 6, as indicated by arrow 8, and out through outlet 24, as indicated by arrow 10. Preferably, at least one, and preferably a plurality of, perfusion compartments 18 are disposed in the flow path of chamber 4. Each compartment 18 is defined by at least one, and preferably a plurality of, porous membranes 19. Each compartment 18 contains at least one, and preferably a collection of, micro-organ cultures 20, such as a liver micro-organ culture. There are one or more brackets 16 attached to mounting clamps 14 or other mounting means which hold perfusion compartments 18 in the fluid path of chamber 4. Preferably, a baffle 22 directs the flow of fluid within chamber 4. The direction of fluid flow within chamber 4 is indicated with arrows. Also preferably, a returner 21 is included for returning at least one product of collection of micro-organ cultures 20 to the subject (not shown).

Figure 1D:
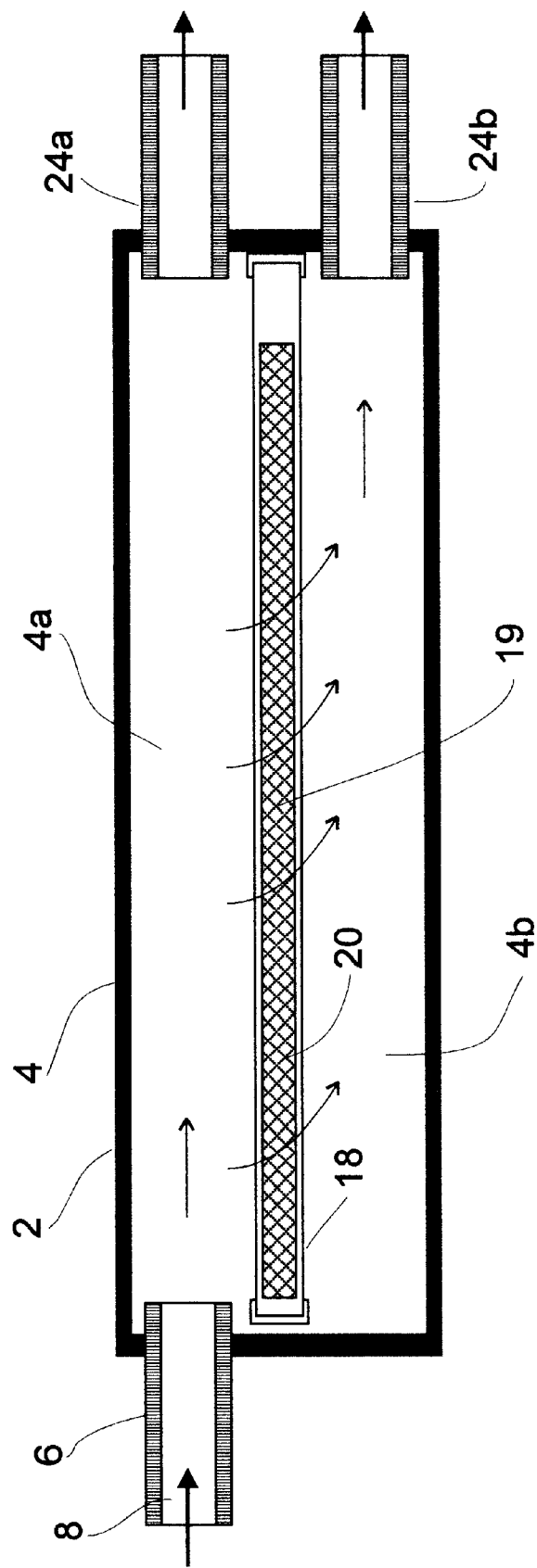

In the embodiment set forth in FIGS. 1A–1C, the flow path and pressure about each of perfusion compartments 18 is substantially homogenous. Accordingly, diffusion across porous membrane 19 into compartment 18 is limited by simple boundary diffusion principles such as concentration gradients, brownian motion, etc. Where such diffusion is insufficient, the rate of fluid permeation into chamber 4 can be increased, as for example, by application of a pressure differential across compartment 18. For example, FIG. 1D shows bioreactor 2 of FIG. 1A reconfigured to provide two distinct flow paths in chamber 4, a "fluid" compartment 4A and a "filtrate" compartment 4B, with fluid communication occurring only through perfusion compartment 18 and consequently through collection of micro-organ culture 20. In the illustrated bioreactor 2, a pressure differential can be created across perfusion compartment 18, for example, by restricting the flow rate downstream of fluid output 24A such as by the use of a valve. A positive pressure differential ($P_{fluid} - P_{filtrate}$) will create a fluid flow from fluid compartment 4A to filtrate compartment 4B, permitting fluid passing though chamber 4 to be in communication with, and thus biologically modified by, collection of micro-organ cultures 20. In general, output 24B from the filtrate compartment 4B is preferably remixed with output 24A from the fluid chamber 4A before returning to the subject.

Suitable matrix materials for forming the micro-organ perfusion compartment include polyamides including nylon such as polycaprolactam and polyhexamethylene adipate, polyamide-imides, polycarbonates, polyacrylates including polymethyl methacrylate and polyethylmethacrylate and polystyrene. For some applications, suitable matrix materials may also be keratin (silk wool, hair), collagen, of various types, polyolefins such as polyethylene, polypropylene and polybutylene, polyesters such as polyethylene terephthalate and polyethylene adipate, polyurethanes such as polyesterurethanes and polyetherurethanes, glass including glass fibers, stainless steel, silicones, organopolysiloxanes and graphite and combinations thereof The keratin matrix is keratin, keratin-containing or keratin-like. Others are known in the art. See, for example, U.S. Pat. No. 5,344,454; U.S. Pat. No. 4,883,666; U.S. Pat. Nos. 4,892,538 and 5,106,627; U.S. Pat. No. 4,391,909; and U.S. Pat. No. 4,353,888.

Preferably, collection of micro-organ cultures 20 will be encapsulated in a semi-permeable matrix forming an isolatory chamber, such as may be formed from a variety of semi-permeable materials known in the art. The membrane or the like allows passage of nutrients and small vital molecules including oxygen, glucose and hormones between the micro-organ culture and the fluid being treated, but does not allow passage of agents of the immune system such as white cells and, if required, antibodies. As used herein, the term "particle" includes molecules, cells and proteins.

More particularly, when the micro-organ culture is derived from another animal species (i.e., xenogenic with respect to the subject being treated), the pore size must be sufficient to prevent the passage of both inflammatory cells and molecular immunogenic factors from the host into the implant tissue chamber. As used in this specification, "molecular immunogenic factors" refers to molecules such as antibodies and complement. Pore sizes sufficient to block passage of both inflammatory cells and molecular immunogenic factors in humans lie in the range of about 0.015 micron. When the micro-organ cultures are from the same animal species but having a different genetic make up (i.e., allogenic), the pore size usually must be sufficient only to prevent the passage of inflammatory cells from the host into the implant cell chamber. Pore sizes sufficient to block passage of inflammatory cells in humans lie in the range of below about 0.8 micron. In most embodiments, it is desirable that the micro-organ culture be provided in an immunoisolatory compartment, e.g., the pore size and membrane thickness will be selected to provide a molecular weight (MW) cutoff of about 40,000 Da to about 250,000 Da, such that the molecules which are able to pass have a molecular weight less than from about 40,000 Da to about 250,000 Da.

Figure 2A:
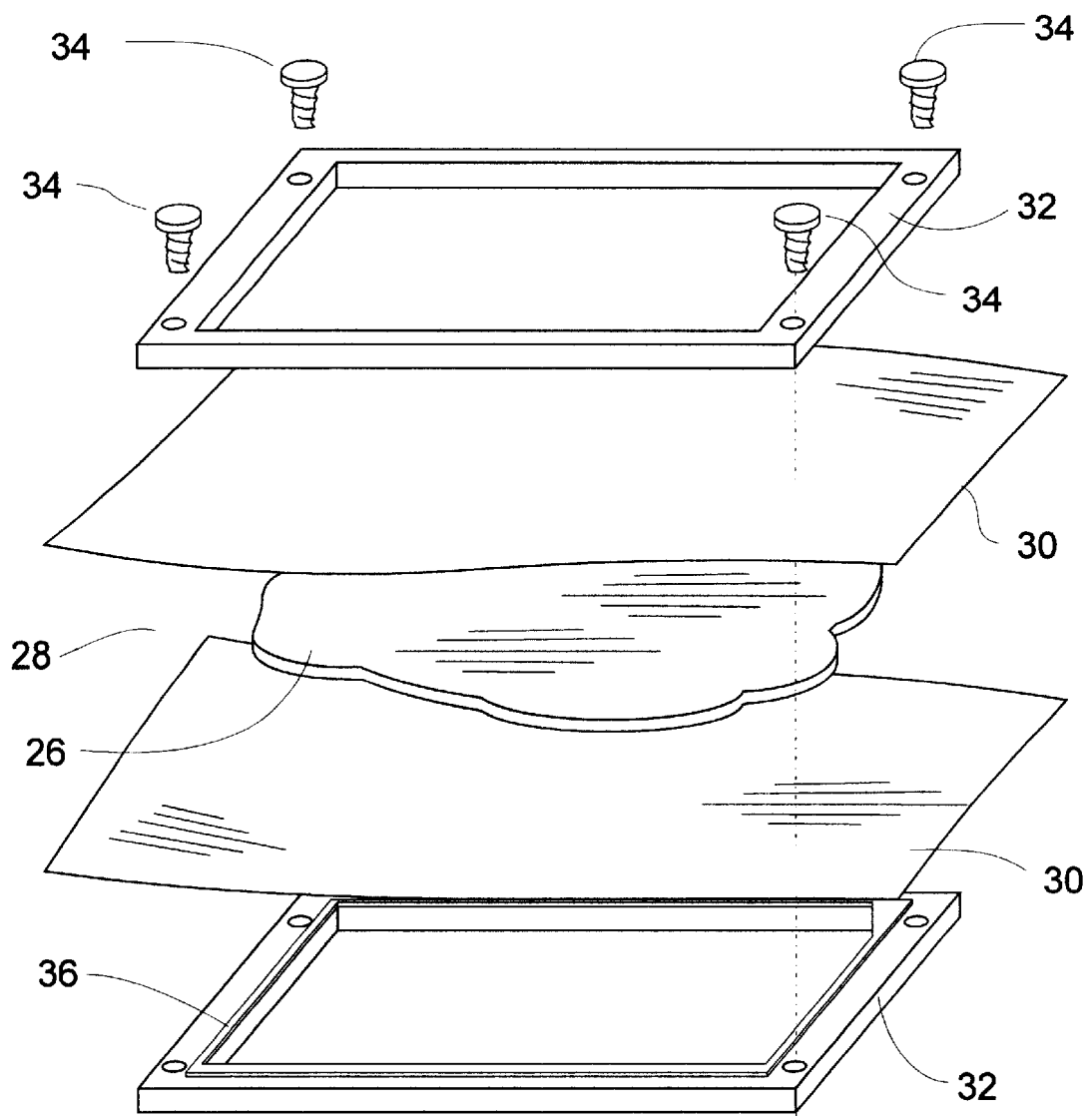
FIGS. 2A and 2B are diagrammatic sketches of an immunoisolatory compartment for a micro-organ culture.
Figure 2B:
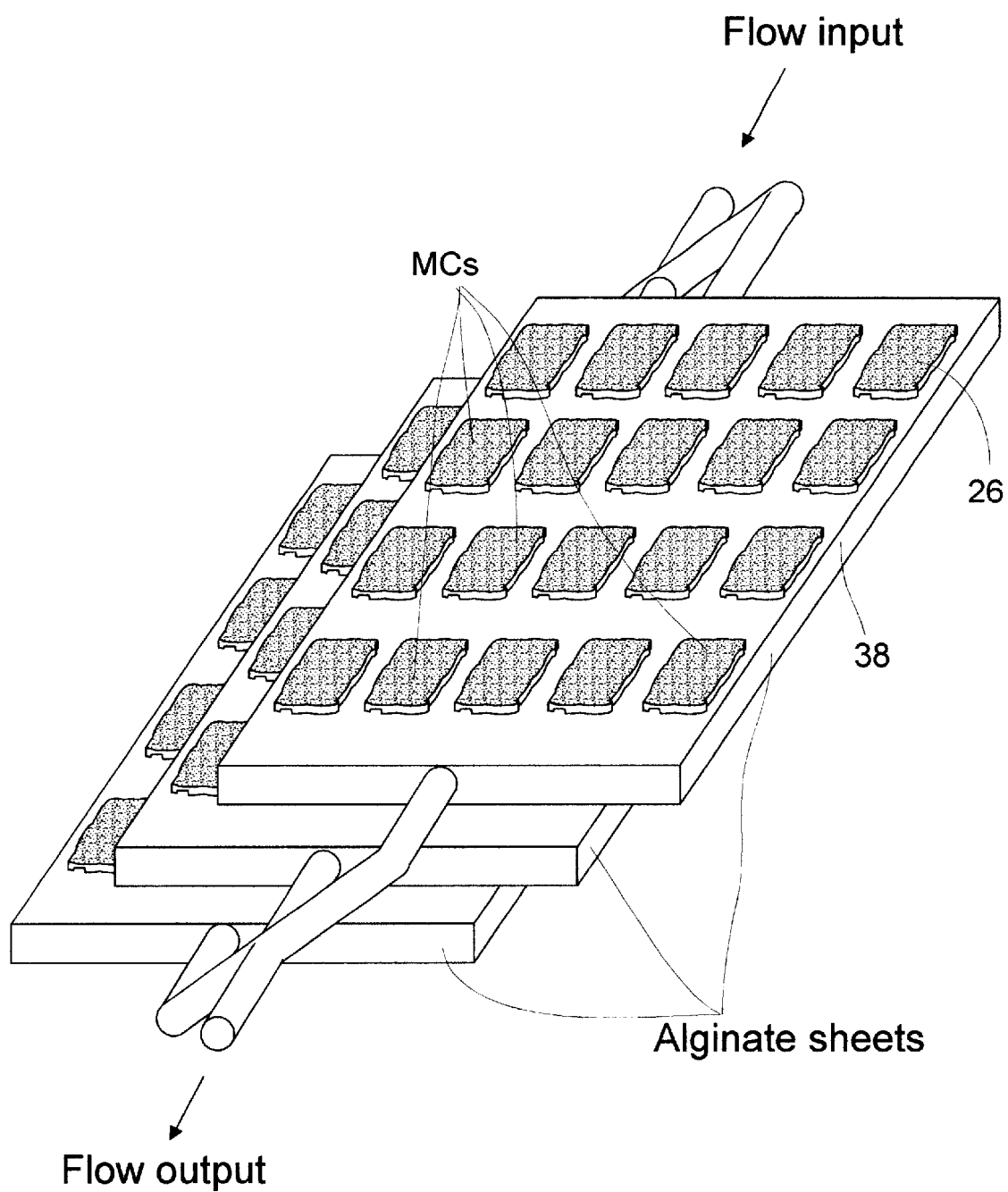

As an illustrative embodiment of such an immunoisolatory compartment, FIG. 2A shows at least one, and preferably a collection of, micro-organ cultures 26 disposed in an immunoisolatory compartment 28 formed by two opposing sheets of semi-permeable membranes 30. Collection of micro-organ cultures 26 are placed between two membrane sheets 30, or encapsulated directly into a membrane sheet as shown below (FIG. 2B). Opposing clamps 32 are fastened together, such as by a screw or screws 34, such that a facing raised ridge 36 of each clamp 32 can be used to create a substantially liquid-proof seal around micro-organ culture 26. Alternatively and preferably, in place of clamps 32, the edges of membrane sheets 30 can be sealed by glue, heat, sonic welding, or other sealing techniques suitable from the art.

More preferably, collection of micro-organ cultures 26 is encapsulated directly into a planar alginate sheet of specified dimensions. Such a configuration is shown in FIG. 2B, with a plurality of planar alginate sheets 38. As an example, a planar alginate sheet having a first dimension of about 40 cm, a second dimension of about 60 cm and a third dimension of about 350 micrometers can be prepared. Each such sheet could contain about $1-2 \times 10^{10}$ cells. Thus, in order to obtain approximately the same number of cells as a human liver, for example, the number of required sheets would be in a range of from about 4 to about 10 sheets.

It will be evident that other configurations of the fluid/filtrate embodiment of the subject bioreactor can be provided for multiple perfusion compartment systems. These configurations can be also be used with one of the sheet configurations described above.

Figure 3A:
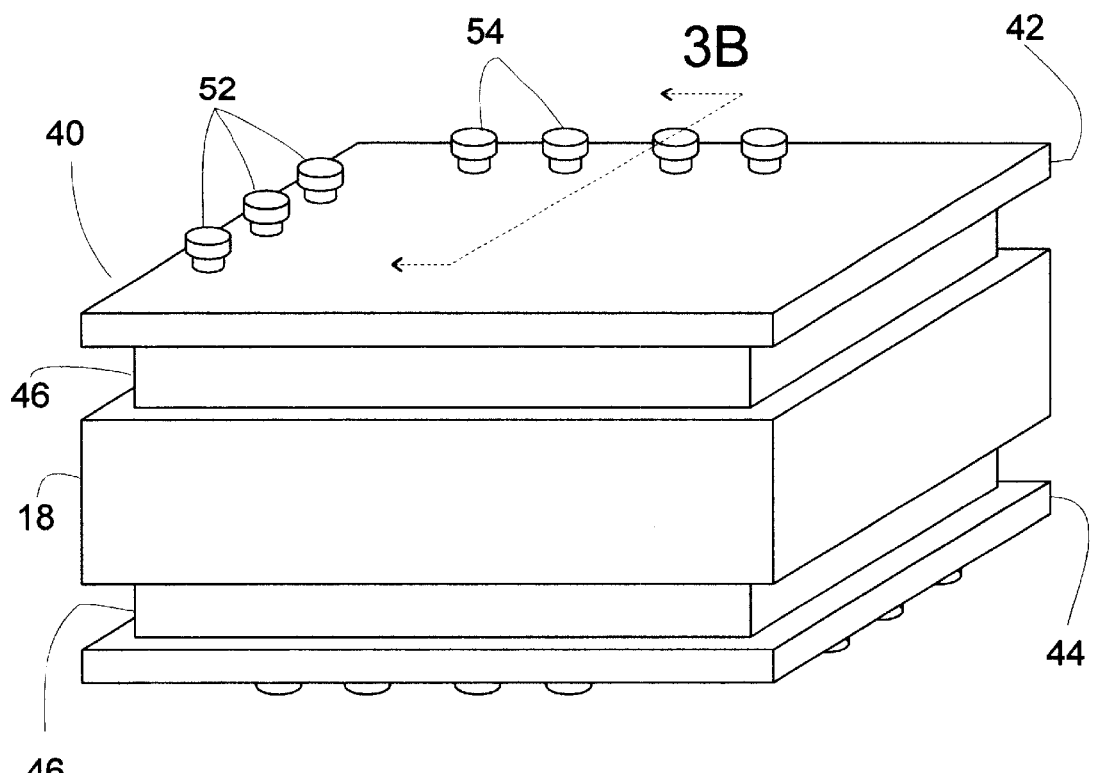
FIGS. 3A–3C are diagrammatic sketches of a second bioreactor of the present invention.
Figure 3B:
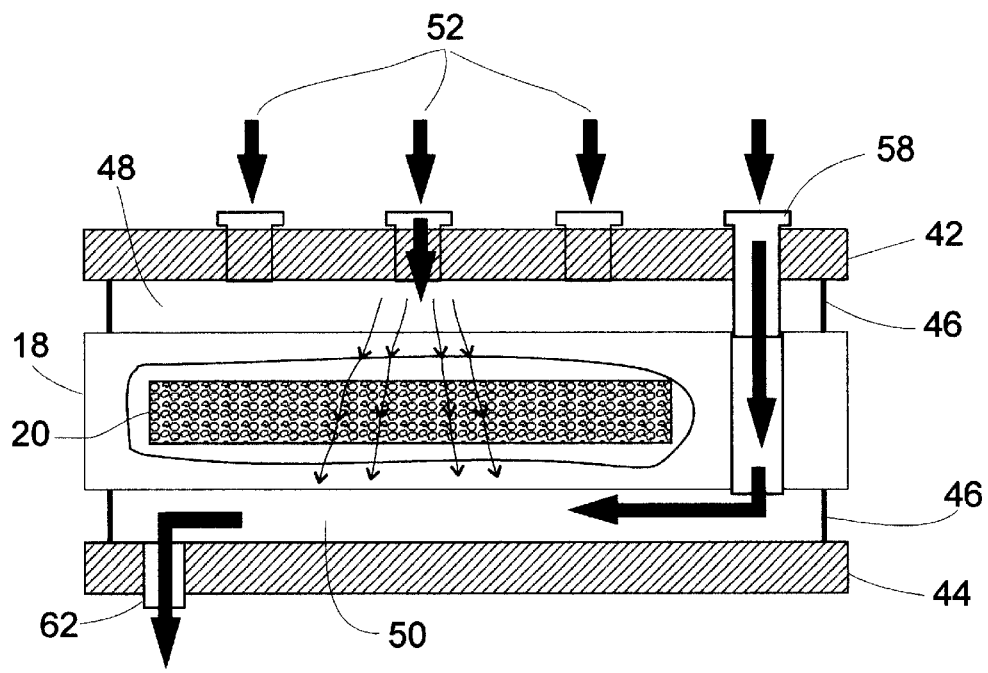
Figure 3C:
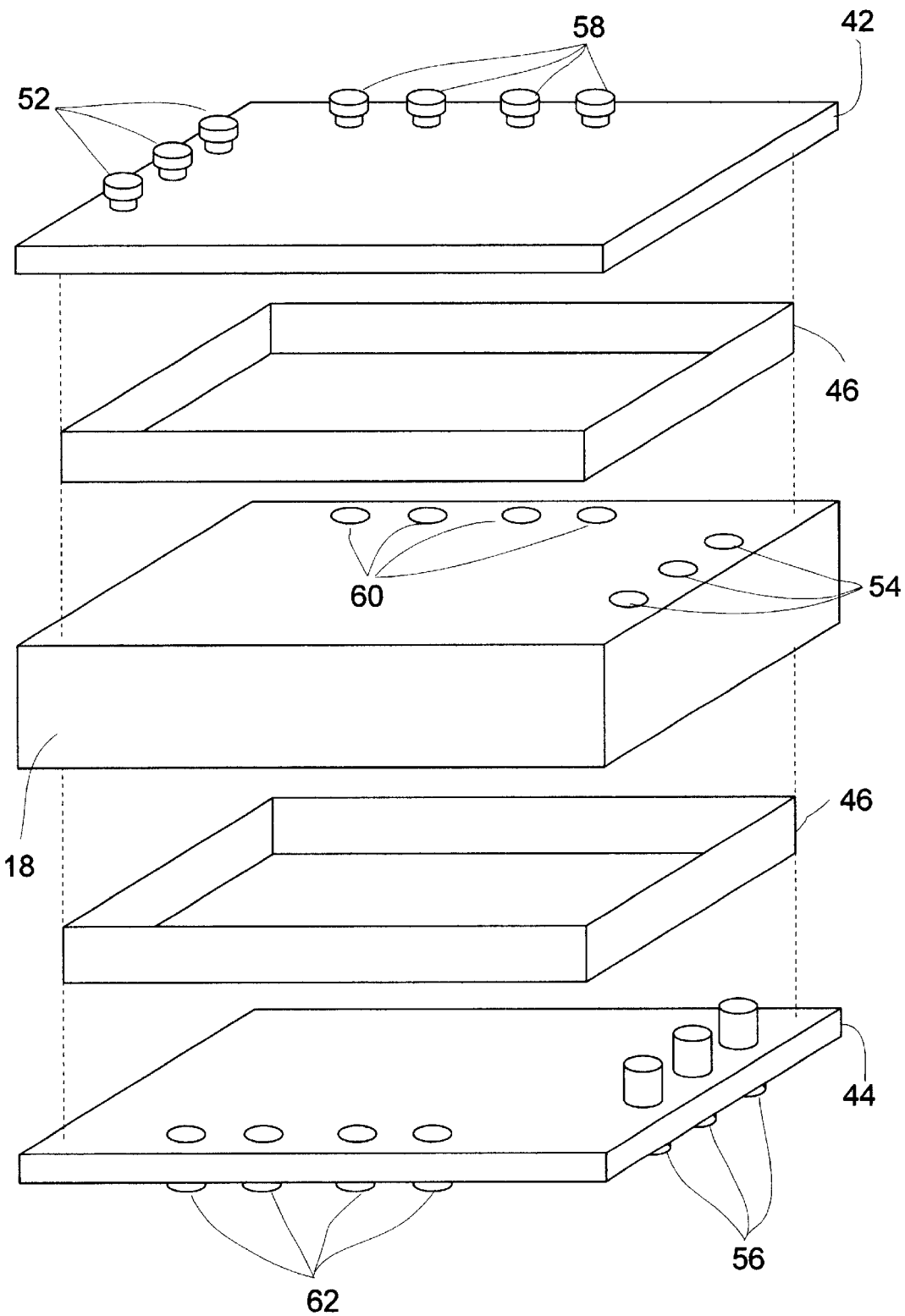

For instance, FIGS. 3A–3C illustrate a basic cartridge 40 which can be linked in tandem with other cartridges 40 to form a bioreactor (not shown) with multiple perfusion chambers. In the exemplary embodiment, a collection of micro-organ cultures 20 is disposed in a perfusion compartment 18. By sandwiching perfusion compartment 18 between two end plates 42 and 44, with at least one spacer 46 provided therebetween, a fluid compartment 48 and a filtrate compartment 50 can be created on opposing sides of perfusion compartment 18.

In operation, fluid entering by at least one, and preferably a plurality of, fluid inputs 52 can flow through fluid compartment 48, and accordingly along a permeable surface of perfusion compartment 18, exiting fluid compartment 48 via at least one, and preferably a plurality of, fluid ducts 54 which are bores running transversely through perfusion compartment 18. The fluid provided by fluid ducts 54 then exits cartridge 40 via at least one, and preferably a plurality of, fluid outlets 56, which do not permit contact with any fluid in filtrate compartment 50. In a similar fashion, filtrate fluid entering at least one, and preferably a plurality of, filtrate inputs 58 is communicated directly to at least one, and preferably a plurality of, filtrate ducts 60 without contact with any other fluid in the fluid compartment 48.

However, filtrate ducts 60 discharge the filtrate fluid into filtrate compartment 50, where it is in direct contact with another (permeable) surface of perfusion compartment 18. Dialysate exits compartment 50 via at least one, and preferably a plurality of, filtrate outputs 62. It will be evident from the present description that fluid from fluid compartment 48 can also permeate perfusion compartment 18, be acted upon by collection of micro-organ cultures 20, and be returned to filtrate compartment 50 as the metabolic derivative.

In practice, cartridges 40 can be arranged in tandem by rotating the second of two adjacent cartridges by 180° such that fluid inputs 52 and filtrate inputs 58 of a second cartridge 40 are aligned with fluid outputs 56 and filtrate outputs 62, respectively, of a first cartridge 40. Repeating this assembly can provide for a multitude of sequentially linked cartridges 40 having, effectively, one fluid chamber and one filtrate chamber with multiple micro-organ cultures disposed therebetween. By capping, or otherwise sealing the filtrate inputs for first cartridge 40 of the series, the flow of fluid provided in the filtrate compartment is the result of treated fluid exiting the perfusion chamber.

Figure 4:
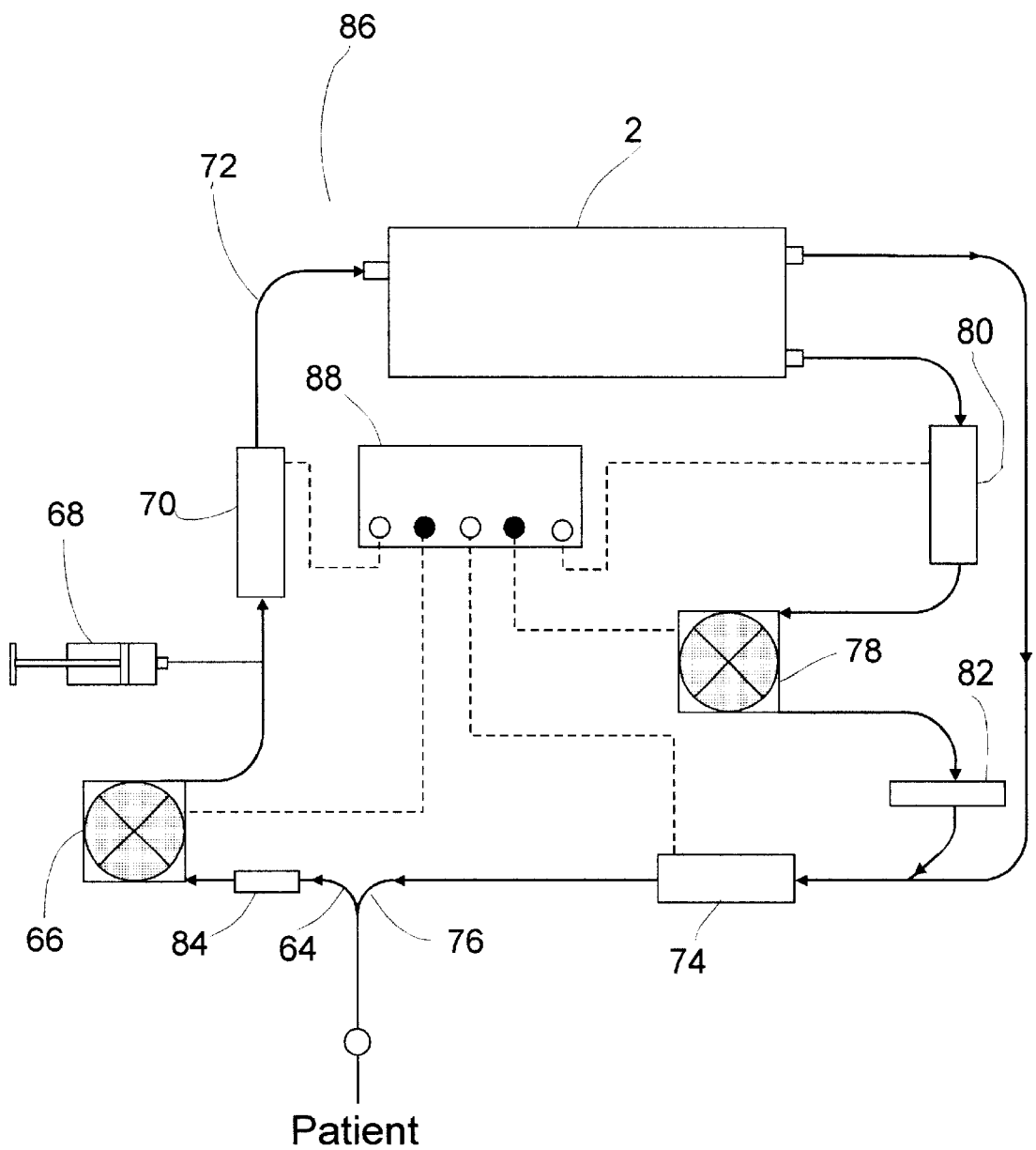
FIG. 4 is a diagrammatic sketch of an exemplary operational circuit for a device employing a bioreactor as shown in FIGS. 1 or 3.

FIG. 4 further illustrates the use of the above described bioreactors 2 of FIGS. 1–3 in the device of the present invention. For ease of understanding, the preferred embodiments are described in terms of a liver assist device (ELAD) utilizing liver micro-organ cultures. However, as described above, other organ augmentation can be carried out with the device of the present invention.

FIG. 4 shows another embodiment of the device of the present invention, which preferably includes bioreactor 2 of FIGS. 1D, 2B or 3A–3C. This embodiment is intended as an example only and is not meant to be limiting. The method of use of this embodiment is also given.

An arterial tube 64 is shown through which blood is delivered from a double lumen venous catheter (or the like) from the subject. Blood flow into the ELAD system is preferably controlled, for example, by a peristaltic pump 66. An anticoagulant, e.g., heparin or the like, is preferably delivered to arterial tube 64 by a syringe 68. Urea, clotting factors, other hepatocyte derived proteins or conversion products, or the like may also be added to the blood. The blood enters an arterial drip chamber 70, where the precolumn pressure (PI) is monitored. Blood passes out of drip chamber 70 and into bioreactor 2, so that bioreactor 2 (which is the chamber containing the collection of micro-organ cultures here) is perfused with blood from the subject. If desired, a filter or the like (e.g., a commercially available 1 mm mesh filter) may be positioned between drip chamber 70 and bioreactor 2 to prevent clogging of the device. Bioreactor 2 has an inlet tubing set 72 to which the blood from arterial tube 64, with or without the anticoagulant, is delivered. Bioreactor 2, and specifically the collection of micro-organ cultures contained within, processes the blood.

During the passage through bioreactor 2, molecules, preferably of a size of from about 10,000 Da to about 250,000 Da, and most preferably of from about 60,000 Da to about 80,000 Da, are able to diffuse across an immunoisolatory membrane and are exposed to the micro-organ culture. No cellular material from the blood comes into direct contact with the micro-organ culture. Small molecules and proteins less than the molecular weight cutoff pass back into the blood.

Bioreactor 2 delivers the processed (e.g., modified or detoxified) blood to a venous drip chamber 74, which may be part of an air-in-blood detector, and to a venous tube 76. Moreover, the system can monitor pressure in drip chamber 74, which is venous pressure (Pv). Accordingly, the column pressure (PI−Pv) can be calculated.

Plasma is ultrafiltered through the micro-organ culture, preferably simultaneously with blood flow through bioreactor 2,. A pump 78 draws plasma across the micro-organ culture chamber and into the filtrate chamber, where it is collected and passes into a filtrate drip chamber 80 and then through a cell filter element 82, e.g., a 0.45 µm filter, which is provided to ensure that cells or large molecules do not pass into the subject. The pressure (P2) in this chamber 80 is measured, and the membrane pressure (PI−P2) is thus provided. Filter 82 senses and contains any leakage of cells from the micro-organ culture. The filtrate is then remixed with the blood flow from bioreactor 2.

Preferably, the outlet of filter 82 is connected to a first three-port (e.g., Y-shaped or T-shaped) tubing fitting having a fitting for an oxygenator line at one end for connection to an oxygenator so that the fluid is oxygenated.

The filtrate circuit illustrated in FIG. 4 accordingly provides for a positive pressure differential across the micro-organ culture compartment in order to enhance flow of serum through the micro-organ culture. Preferably, a pressure sensor 84 can also be situated in-line between arterial tube 64 and syringe 68. Pressure sensor 84 may monitor the pressure of the arterial blood being pumped from the subject to bioreactor 2. Additionally and preferably, a pressure sensor may monitor pressures at the inlet tubing connected to bioreactor 2 after heparin or a like anti-coagulant is pumped into the arterial line. Other pressure sensors are preferably included at the outlet venous line to measure the return of fluid to the subject, as well as in the recirculation tubing set at various locations for added safety. Thus, the pressure sensors allow for the monitoring of both the access and return pressures of the subject, and the pressure across the device to detect plugging or rupture problems thereof. Furthermore, pressure sensors on each side of filter 82 can monitor for any release of cellular or large particles from the device.

A complete tubing set 86 includes all of the tubing used in the above embodiment. Preferably, tubing set 86 is produced from extruded polyvinylchloride (PVC) tubing or the like of the grade typically employed in systems utilized in hemodialysis, therapeutic plasma exchange, and open heart surgery. The pump segments of the tubing preferably are designed to operate at a blood flow rate of approximately 100 ml/minute to 500 ml/minute, and preferably 250 ml/minute, for approximately 120 hours without developing failure resulting in loss of blood by the subject. The molded parts utilized in tubing set 86 can comprise rigid PVC, Lexan HP resin or other like material and are designed to exhibit long term high strength bonds to PVC tubing in an environment consistent with uses described above. The sterilization method for tubing set 86 includes ethylene oxide to yield sterilization of tubing set 86.

As is farther shown in FIG. 4, a control system 88 controls the overall system operation. Control system 88 may include a number of modules in a single integrated system, or as separate modules. One of the modules operates the dual pump system. Such control modules are commercially available (e.g., a BSM-22 Dual Pump Blood Safety Module commercially available from CGH, Inc. of Lakewood, Colo.).

Another module of control system 88 is an auxiliary monitoring unit (AMU) which is designed to monitor pressures, accept alarm settings from the operator by a keypad or the like, and, in turn, notify the operator if certain alarm limits are reached.

A third module of control system 88 is a Venous Pressure Monitor (VPM) which monitors the pressure in the venous return to the subject in an extracorporeal circuit during treatment. The VPM, also commercially available from CGH, Inc., may include two types of alarms. A first type of alarm has a limits window such that the alarm is triggered when the pressure value is 40 mmHg or lower or 70 mmHg or greater than the selected value. A second alarm is a so-called "out-of-range alarm" in which the alarm is triggered when the pressure value is higher than +450 mmHg or lower than +10 mmHg. When an alarm is activated, the blood pump stops. The VPM includes pressure transducing elements and a power supply.

The tubing and connections thereof of the illustrative device are preferably capable of withstanding positive pressure (lumen to exterior) of 3 atmospheres (2,300 mmHg) and negative pressure of 0.75 atmospheres without suffering catastrophic failure or developing leaks between the interior and exterior of the tubing set. This design results from the consideration that the typical pumps and tubing, used for extracorporeal treatment, reach their delivery limits at about 0.7 atmospheres negative pressure and 1.5 atmospheres positive pressure. The pressure limits established bracket these limits and provide a reasonable safety margin.

The blood flow rate is preferably adjustable within the range of 0 to 500 mls/minute. The rationale for this is several fold. It is well established that continuous hemodialysis is effective at blood flows of 150 mls/minute. This is to be contrasted with the resting normal renal flow rate of about 1,000 mls/minute. It is believed that the liver has less reserve capacity than the kidneys, and hence the maximum flow rate is a higher fraction of the resting normal hepatic blood flow rate of about 1,500 ml/minute. It is also well established that such extracorporeal flow rates are achievable with standard blood access devices, e.g. single or dual lumen subclavian catheters. With higher blood flow rates, the therapeutic effect may be enhanced.

The recirculation flow, e.g., the extraction flow rate, for the recirculation tubing set is between about 5 ml/min to about 120 ml/minute, and preferably from about 20 ml/min to about 80 ml/min. This flow can also be defined in terms of a fraction of the blood flow. For example, the extraction flow rate is within a range of from about 5% to about 30% of the blood flow rate, and preferably from about 10% to about 20% of the blood flow rate. The operator is preferably provided with a table of recirculation flow rates correlated with blood flow rates, or alternatively it is envisioned that such could preferably be stored in a memory of controller 88.

Additionally or alternatively, and preferably, if blood is the fluid being biologically modified, a hemoglobin detector may be utilized in the filtration circuit to indicate any leaks across the micro-organ culture chamber or chambers. The hemoglobin detector can also serve to indicate any loss of cells or particles from the extracapillary space as these cells scatter the light and reduce the monitor's output correspondingly. Further, the hemoglobin monitor can be coupled to various alarm circuits to indicate that operator attention is required. The pressure sensors can be incorporated into similar alarm systems, or have an alarm system dedicated thereto. Both the hemoglobin detector and the pressure sensors can be coupled to a controller, and can be used to shut down one or more pumps of the closed loop system. The optical hemoglobin detector is preferably capable of detecting blood losses to the recirculation line of 1 part packed red cells in 60 parts of plasma. This detection method should preferably operate for both losses which result in intact red cells in the detector or for the specified quantity of cells totally hemolyzed.

Furthermore, the system configuration can be modified to include an arteriovenous fistula in which the pump connected to arterial tube 64 is obviated. Further, the configuration can be adapted for use with a single needle access by adding a reservoir at either end of bioreactor 2 and including a blood pump on the return line.

To establish operation of the device of the present invention, ordinary medical procedures are conducted, and equipment setup is believed to be well within the grasp of the ordinarily skilled artisan. Briefly, the operator responsible for the setup of the equipment will load tubing set 86 onto control unit 88, appropriately thread the pump headers into pumps 66 and 78 (if present), attach the pressure monitoring tubing to pressure monitor 74 (if present), set the alarm settings to the values appropriate to the priming mode, fill the anticoagulant (e.g., heparin) syringe 68 with the prescribed heparin dosage, attach heparin syringe 68 to tubing 72, secure heparin syringe 68 to control unit 88, and attach the priming solution to arterial tube 64. The priming solution may be normal saline.

For blood access, the physician in charge of the procedure will establish an appropriate procedure and perform the blood access. This blood access must be capable of delivering the blood flow rate mentioned above required to achieve the desired therapeutic input upon the subject. This blood access must be appropriately anticoagulated by heparin or the like as discussed above. The principles of operation of the device of the present invention depend upon unhindered passage of certain blood borne materials to the perfusion compartment housing micro-organ cultures and similar passage of solutes from the micro-organ cultures to the blood. Compromising this carrying capacity due to inadequate anticoagulation is to be avoided. Of particular concern at the initiation of circulation is coagulation created by stasis within the access during preparation.

The first connection to be made is the subject access line e.g., arterial tube 64. The priming solution is ported into arterial tube 64 at a rate sufficient to ensure that return tube 76 and return line connection are free of trapped air. When the connection is made, flow of priming solution is halted so that the physician can manipulate the tubing to ensure that there is not an unacceptable amount of air at the connection. Arterial tube 64 is then connected.

To initiate the procedure, pump 66 is started. Venous tube 76 is unclamped, and heparin is injected. The pressure monitoring chamber levels are examined and adjusted if necessary. To continue the procedure, the operator or attendant personnel should periodically examine the fittings for leaks, the bypass tubing set for evidence of blood cell accumulation, and the monitoring chambers for appropriate levels. The monitoring chamber levels should be readjusted if they vary by more than 0.5 cm from the nominal level, the nominal level being 50% or higher of the drip chamber. Frequent adjustment of a given monitoring chamber level should motivate the operator to thoroughly examine the tubing for minute leaks. Syringe 68 should be monitored for the amount of anticoagulant remaining and replaced as appropriate.

When the procedure is to be terminated, and the setup broken down, pump 66, and the heparin injection are stopped in turn, and arterial tube 64 clamped. The blood remaining in the system is returned to the subject per protocol using either fluid or air displacement, and venous tube 76 clamped. At this point, control unit 88 with attached tubing set 86 and therapeutic device can be removed from the intensive care unit or area in which it has been used.

The above description centered upon the device and method of the present invention. Below are examples of successful preparation of micro-organ cultures which could be used with the device and method of the present invention, as well as an example of in vivo use of the device of the present invention. These examples are intended for illustrative purposes only and are not limiting.

As described in the illustrative examples below, micro-organ cultures from liver, have been isolated and grown for up to 48 days in culture. However, it is within the scope of the invention to maintain cultures for extended periods of time beyond 48 days.

EXAMPLE 1

Preparation of liver Micro-Organ Cultures

Mouse micro-organ cultures from liver were prepared as follows. Organs were removed and with scissors, were cut to an appropriate width of 2 mm, length of 3 mm and sliced using a tissue chopper or other suitable cutting means into sections of 300 micrometers thick. These microorgans were placed in a 24-well microplate in 400ml of Dulbeco Minimal Essential Medium (DMEM) in the absence of fetal calf serum (FCS) under 5% CO2 at 37° C., under constant shaking at 12 rpm for periods of one to eight days. Twenty micro-explants were grown per well.

EXAMPLE 2

Measurement of Cell Proliferation in Liver Micro-organ Cultures

Figure 5:
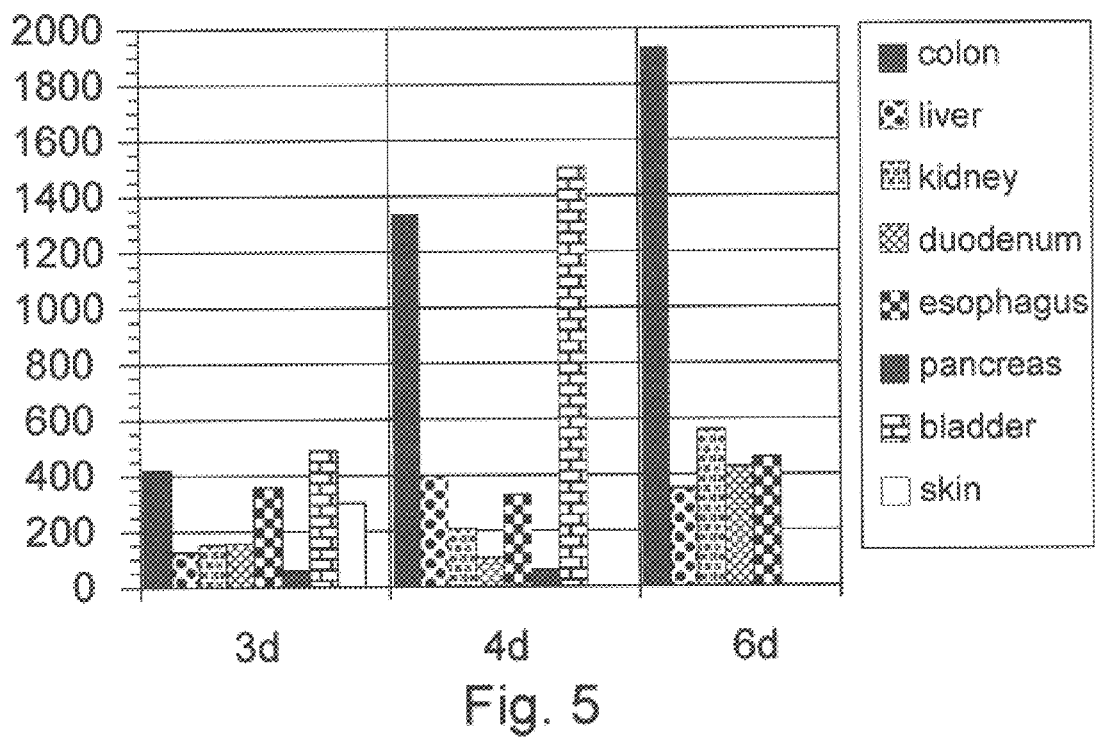
FIG. 5 shows the measurement of cell proliferation in several micro-organ cultures.

Micro-organ cultures from several mouse organs were dissected and cultured in a humidified incubator at 37° C. in the absence of serum using micro-organ cell culture technique, as described in example 1. To assess cell division, incorporation of tritiated thymidine was measured using standard protocols (Kobayashi, et al. (1994, *J Biomater Sci Polym Ed* 6(4):325–42). These results show that DNA synthesis occurs during the culture period (FIG. 5). In addition, mouse liver micro-organ cultures were grown as described in example 1 for 14 days and pulsed for 4 hours with bromodeoxyuridine, fixed, and stained with a fluorescent antibody to bromodeoxyuridine to label mitotic nuclei (Sigma Chemical). Nuclei that are actively synthesizing DNA were observed in these cultures (data not shown).

EXAMPLE 3

Albumin is Produced by Mouse Hepatocytes in Micro-organ Cultures.

Figure 6:
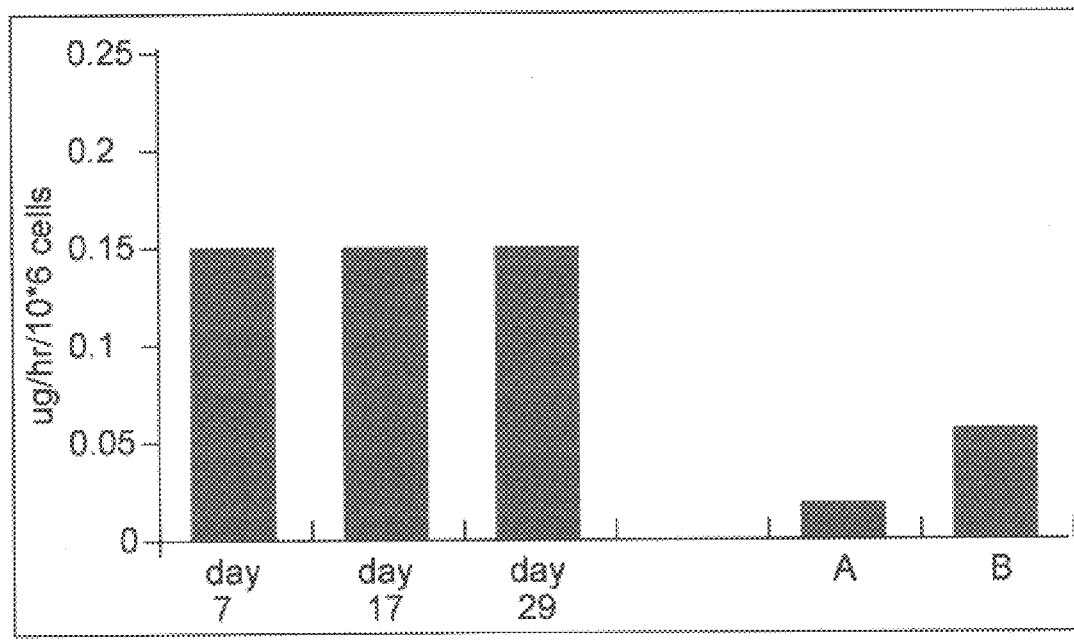
FIG. 6 shows the measurement of albumin produced by mouse hepatocytes in micro-organ cultures.

Primary mouse hepatocytes grown in micro-organ cultures as described in example 1, remain functional for at least four weeks, as assayed by secretion of albumin and production of urea (see FIG. 6). Mouse hepatocytes in micro-organ cultures produce relatively large amounts of albumin as tested both by Eliza and by colorimetric methods (kit No 631, Sigma Chem. Co. St. Louis Mo.). The histogram shown below displays the amount of albumin secreted per $10^6$ cells per hr. Note that even after one month in culture the rate of albumin production remains high, particularly in comparison to two other conventional culture conditions. A is data taken from Nyberg et al. (*Cell Transplant*, 2:441-52, 1993) and B data from Shatford et al. (*J. Surg. Res.*, 53:549–57, 1992).

EXAMPLE 4

Conversion of Ammonia into Urea in Mouse Liver Micro-organ Cultures

Figure 7:
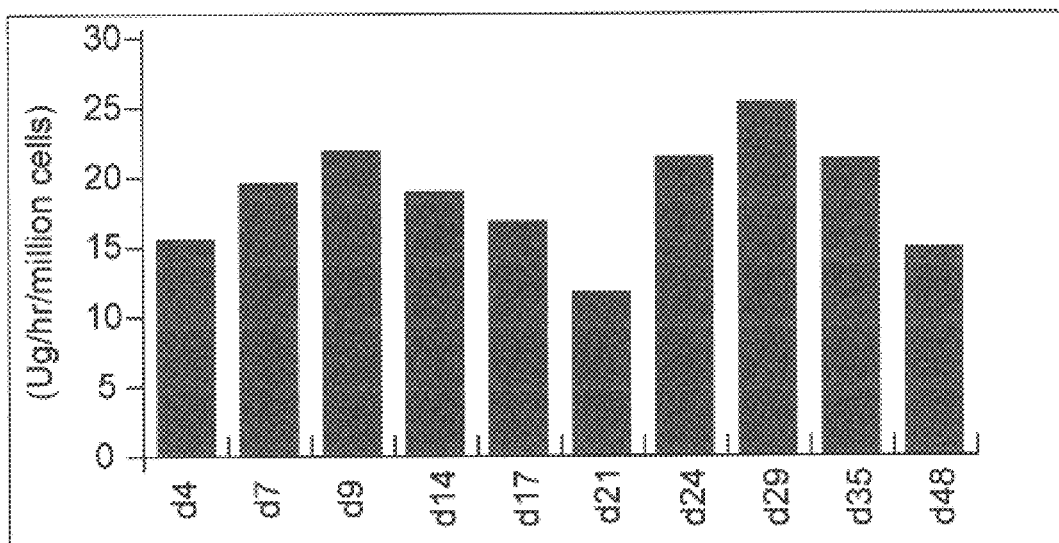
FIG. 7 shows the conversion of ammonia into urea in mouse liver micro-organ cultures.

Mouse liver was dissected and cultured in vitro in the absence of serum or exogenous growth factors using micro-organ cell culture technique as described in example 1. Urea and ammonia were measured from supernatants using standard colorimetric methods using a Urea-Nitrogen kit No 640-A (Sigma Chem Co. St. Louis Mo.). The data shown in FIG. 7 indicates that mouse hepatocytes in micro-organ cultures produce large amounts of urea even after 48 days in culture. As a comparison, Dixit et al. (*Transplantation*, 55:616–22, 1993) have reported values of urea synthesis of 14.6 mg/hr/million cells after 1 day in culture and values of 11.7 mg/hr/million cells after 10 days in culture for micro encapsulated rat hepatocytes in vitro.

EXAMPLE 5

Human Micro-organ Liver Cultures Convert Large Amounts of Ammonia into Urea for Long Periods of Time.

Figure 8:
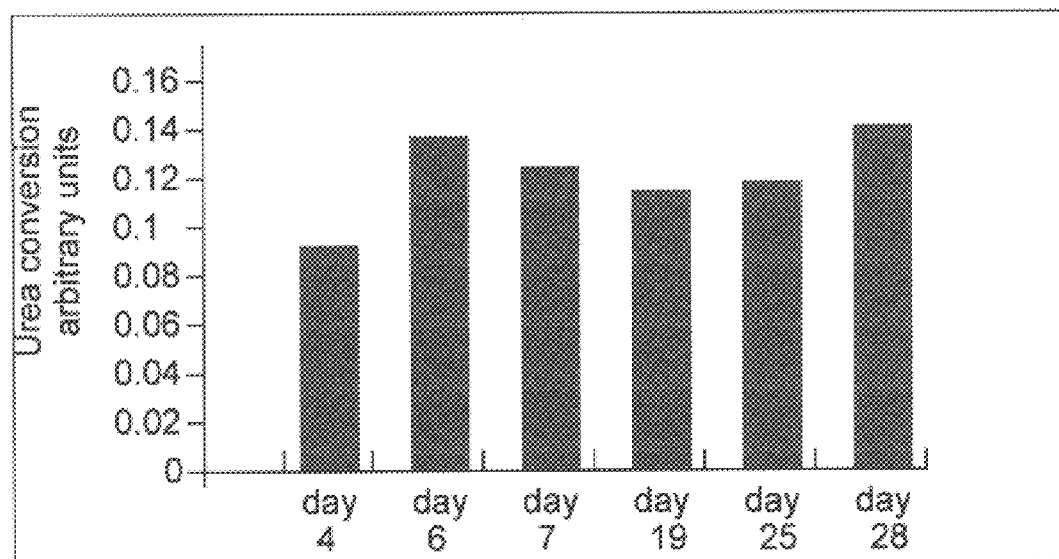
FIG. 8 shows that human micro-organ liver cultures convert large amounts of ammonia into urea for long periods of time.

Human liver micro-organ cultures were prepared as follows. Human liver pieces were obtained from liver wedge biopsies. The pieces were cut to an appropriate width of 2 mm, length of 3 mm, and sliced using a tissue chopper into sections of 300 micrometers thick. These pieces were placed in a 24-well micro plate in 0.4 ml of DMEM in the presence or absence of fetal calf serum (FCS) under 5.5% $CO_2$ at 37° C., under constant shaking at 12 rpm. Twenty micro-explants were grown per well. Every two days the medium was changed and a sample was taken for determination of urea and ammonia. FIG. 8 depicts the amount of urea secreted into the medium in arbitrary units but represent values of 10 to 25 micro-grams urea/hr/million cells.

Humans produce 11.2 gr. of urea per day and there are at least $10^{11}$ hepatocytes in a human liver. Thus human hepatocyte cells produce about 5 mg/hr/million cells of urea in vivo. It can be seen that human liver micro-organ cultures convert ammonia into urea at about the same rate, if not higher, in Vitro than the liver cells in the normal in vivo situation.

EXAMPLE 6

Human Liver Micro-organ Cultures are Metabolically Active

Figure 9:
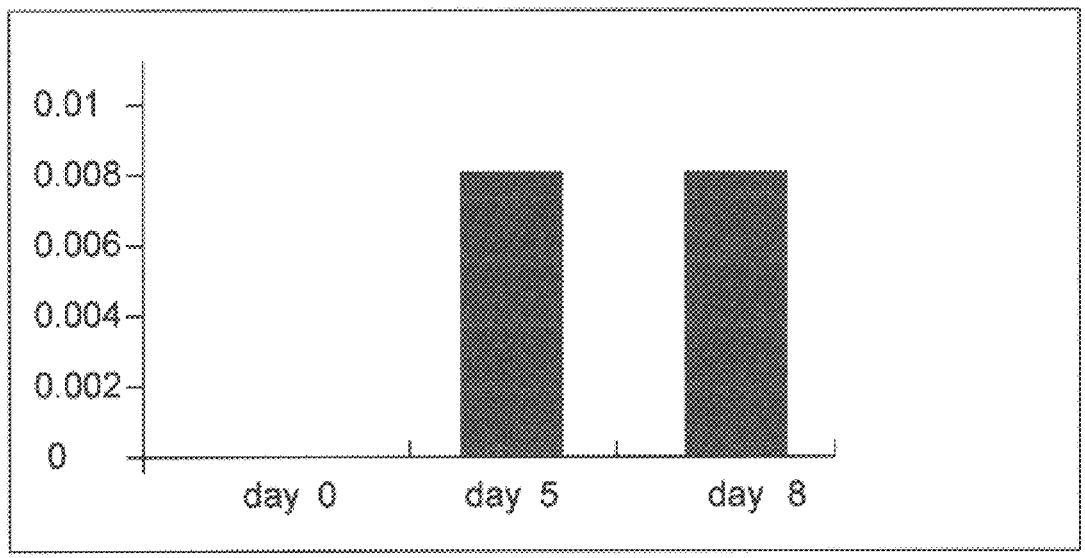
FIG. 9 shows that human liver micro-organ cultures are metabolically active.

Human liver micro-organ cultures were prepared as described in example 5. Results are shown in FIG. 9.

EXAMPLE 7

Cryopreserved Micro-organ Liver Cultures Remain Functional When Grown at 37° C.

Figure 10:
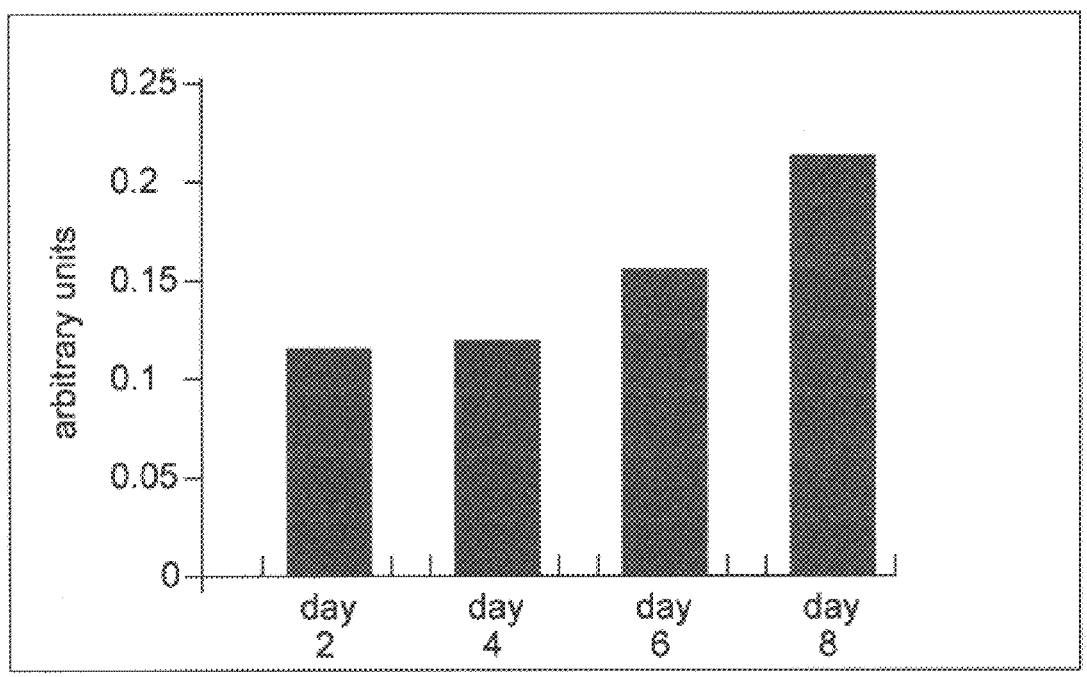
FIG. 10 shows that cryopreserved micro-organ liver cultures remain functional when grown at 37° C.

Micro-organ mouse liver cultures were prepared as described in example 1 and frozen gradually in 10% DMSO to −80° C. and then transferred to liquid nitrogen. After several days, the micro-organ cultures were thawed quickly, rinsed and grown for several days in 10% FCS. As shown in the figure below, liver cells in micro-organ cultures remain viable and functional as determined by their capacity to transform ammonia to urea even after several days in culture . The values obtained are shown in FIG. 10 and are comparable to those obtained from fresh micro-organ cultures grown in similar conditions.

EXAMPLE 8

Cryopreserved Human Micro-organ Liver Cultures Remain Functional When Grown at 37° C.

Figure 11:
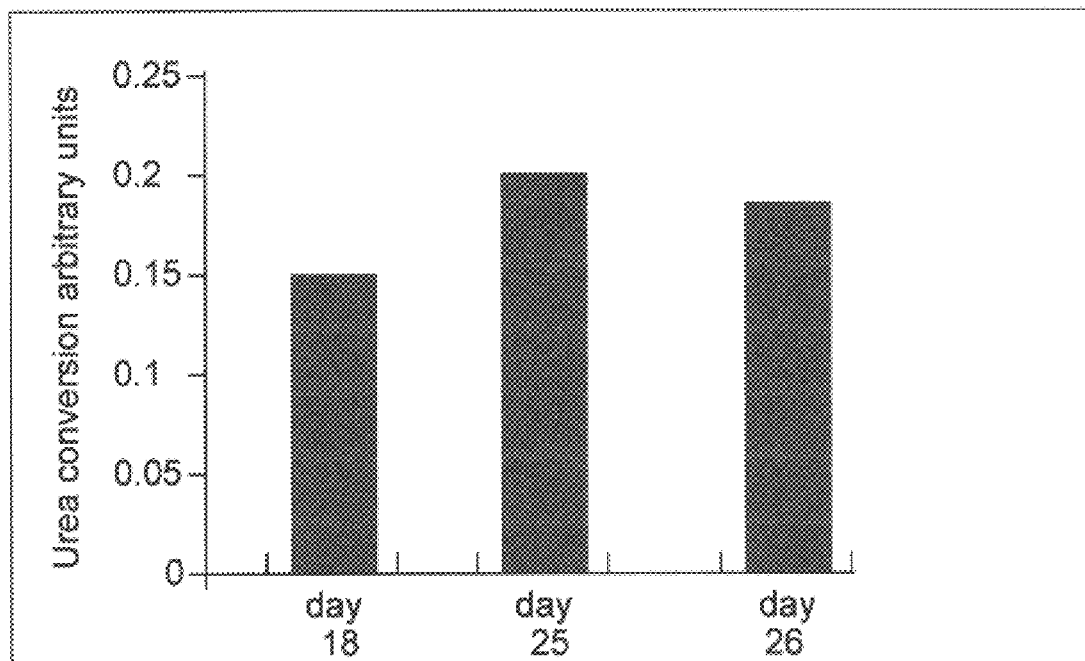
FIG. 11 shows that cryopreserved human micro-organ liver cultures remain functional when grown at 37° C.

Micro-organ human liver cultures were prepared as described in example 5 and frozen gradually in 10% DMSO to −80° C. and then transferred to liquid nitrogen. After several days, the micro-organ cultures were thawed quickly, rinsed and grown for several days in 10% FCS. As shown in FIG. 11, liver cells in micro-organ cultures remain viable and functional as determined by their capacity to transform ammonia to urea even after several days in culture . The values obtained are comparable to those obtained from fresh micro-organ cultures grown in similar conditions.

EXAMPLE 9

Liver Micro-organ Cultures are Metabolically Active When Encapsulated in Alginate Sheets Mouse liver micro-organ cultures were prepared as described in Example 1. Half of them were encapsulated in a thin sheet (about 400 micrometer-thick) made of alginate. The micro-organ cultures encapsulated in alginate sheets were cultured ex vivo in DMEM plus 10% FCS for 12 days.

Figure 12:
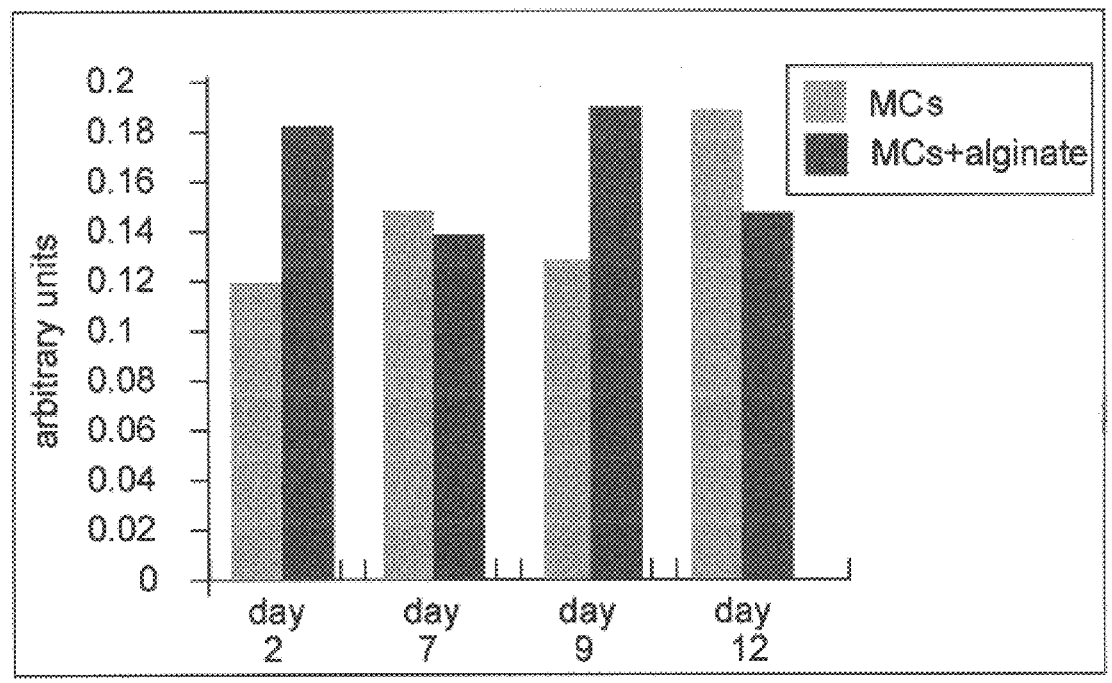
FIG. 12 shows that mouse liver micro-organ cultures are metabolically active when encapsulated in alginate sheets.

Every two days the medium was changed and a sample was taken for determination of urea and ammonia. FIG. 12 depicts the amount of urea secreted into the medium in arbitrary units but represent values of 10 to 15 micro-grams-urea/hr/million cells. Left is micro-organ cultures alone, right is micro-organ cultures in alginate.

EXAMPLE 10

Mouse Liver Micro-organ Cultures Remain Functional When Cultured in 100% Fetal Calf Serum Micro-organ mouse liver cultures were prepared as described in example 1. Half of the cultures were grown in DMEM and 10% FCS (left) and the other half were grown in 100% FCS (right) for five days. Every two days the medium was changed and samples were taken for ammonia and urea determination. Results are shown in FIG. 13 and are particularly relevant because they establish that liver micro-organ cultures not only perform well in in vitro conditions but also in the presence of 100% serum which is nearer to whole blood and often toxic to cells in vitro.

EXAMPLE 11

Rat Liver Micro-organ Cultures Remain Functional When Encapsulated into Planar Alginate Sheets Frozen and Stored at −80° C. and Further Cultured at 37° C.

Mouse liver micro-organ cultures were prepared as described in example 1. Half of them were encapsulated in a thin sheet (about 400 micrometer thick) made of alginate. The micro-organ cultures and the micro-organ cultures encapsulated in alginate sheets were frozen gradually in 10% DMSO to −80° C. and then transferred to liquid nitrogen. After several days, the micro-organ cultures were thawed quickly, rinsed and grown for several days in 10% FCS. Every two days the medium was changed and a sample was taken for determination of urea and ammonia. FIG. 14 depicts the amount of urea (a) and of albumin (b) secreted into the medium in arbitrary units.

EXAMPLE 12

Figure 15:
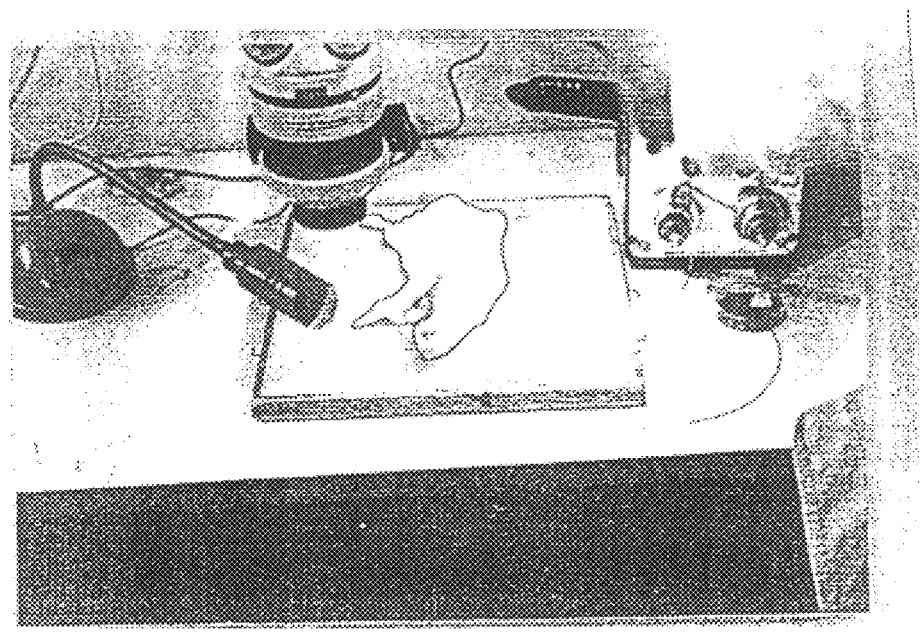
FIG. 15 shows that a normal rat can be safely connected to an example of the device of the present invention.

Normal In Vivo Rats Can be Connected Safely to the Bioreactor Containing Liver Micro-organ Cultures in Alginate Sheets A rat was connected to the prototype described above via cannulation of the right carotid artery and the left jugular vein. Blood was perfused for several hours. Several biochemical parameters were monitored, including of course the well-being of the whole animal. Blood processed by the micro-organ cultures was reintroduced into the jugular vein assisted by a peristaltic pump (see FIG. 15, photograph with rat outlined for clarity). The animal was kept alive for the duration of the experiment, about 8 hours.

EXAMPLE 13

Determination of Optimum Thickness of Liver Micro-organ Cultures

Figure 16:
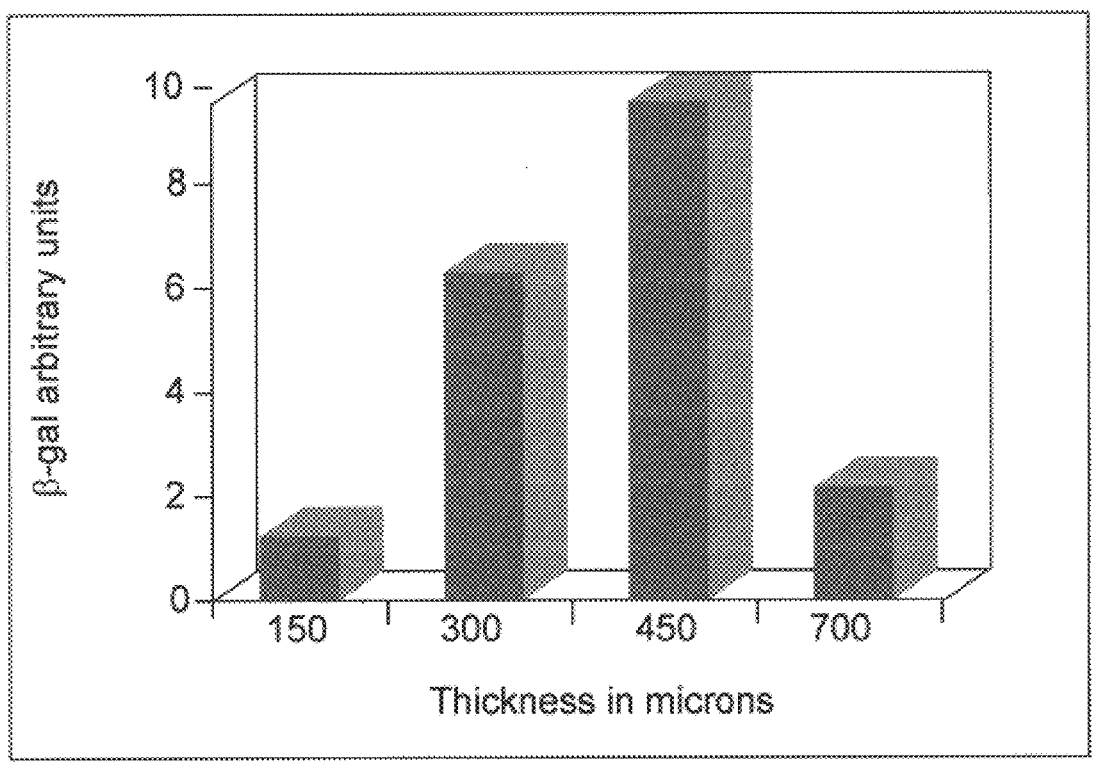
FIG. 16 shows that an optimal thickness of mouse liver micro-organ cultures is 450 micrometers.

Mouse micro-organ cultures from liver were prepared as follows. Organs were removed and with scissors, were cut to an appropriate width of 2 mm, length of 3 mm, and sliced using a tissue chopper or other suitable cutting means into sections of thickness varying from 150 to 700 micrometers thick. These microorgans were placed in 35 mm petri dishes in 2 ml of F12 medium in the presence of 10% fetal calf serum (FCS) under 5% $CO_2$ at 37° C., under constant shaking at 12 rpm for periods of up to three weeks. Each dish contained micro-organ cultures of a given thickness. Every two days samples were removed and were processed for routine histology and urea production. In addition, after six days in culture the micro-organs were transduced with 10 million CFUs/ml of an adeno-derived viral construct engineered to transcribe the lac-z gene (see, *J. Clin. Invest.* 90:2598–2607, 1992) Two weeks after transduction, samples were removed, fixed and processed for recombinant β-galactosidase derived β-gal production. FIG. 16 shows the amount of β-gal production as a function of thickness. Please note that maximal level of production was obtained when 450 micrometers thick micro-culture organs were employed. Similarly, histology and urea production, measured after three weeks in culture, were both optimal for the 450 micrometers thick micro-culture organs as compared with 150, 300 and 700 micrometers thick micro-culture organs.

What is claimed is:

1. A device for performing a biological modification of a fluid, the device comprising:
   (a) a chamber having an inlet for intake of the fluid and an outlet for outflow of the fluid; and
   (b) a collection of liver portions for performing the biological modification of the fluid, each individual liver portion of said collection including liver cells and having dimensions, such that liver cells positioned deepest within said individual liver portion are at least about 150 micrometers and not more than about 225 micrometers away from a nearest surface of said individual liver portion, said collection of liver portions being located within said chamber and said collection of liver portions being in contact with at least a portion of the fluid flowing through said chamber; said collection of liver portions being provided within a continuous liver planar organ formed by coculturing hepatocyte cells in presence of said collection of liver portions, such that said continuous liver planar organ is formed from an admixture of cells derived from said liver portions and said hepatocyte cells.

2. The device according to claim 1, wherein said collection of liver portions is encapsulated by a sheet of a biocompatible polymer, said sheet being located within said chamber.

3. The device according to claim 2, wherein said sheet has a first dimension in a range of from about 30 cm to about 90 cm, a second dimension in a range of from about 30 cm to about 80 cm and a third dimension in a range of from about 300 micrometers to about 900 micrometers.

4. The device according to claim 2, wherein a plurality of said sheets are incorporated substantially parallel in orientation within said chamber.

5. The device according to claim 1, further comprising a porous membrane located substantially within said chamber, said membrane effecting said contact of the fluid and said collection of liver portions.

6. The device according to claim 5, wherein said membrane permits passage therethrough of particles having a molecular weight less than from about 40,000 Da to about 250,000 Da.

7. The device according to claim 5, wherein said membrane restricts passage therethrough of white blood cells, red blood cells and immunoglobulins.

8. The device according to claim 1, further comprising a plurality of tubes for connection to a subject containing the fluid to be biologically modified, at least one of said tubes being connected to said inlet and at least a second of said tubes being connected to said outlet.

9. The device according to claim 1, wherein said collection of liver portions is characterized by being cryopreserved before being located within said chamber.

10. The device according to claim 2, wherein said sheet is characterized by being cryopreserved before being located within said chamber.

11. A device for performing a biological modification of a fluid of a subject, comprising:
   (a) a chamber having an inlet for intake of the fluid and an outlet for outflow of the fluid;
   (b) a collection of liver portions for performing the biological modification of the fluid, each individual liver portion of said collection including liver cells and having dimensions, such that liver cells positioned deepest within said individual liver portion are at least about 150 micrometers and not more than about 225 micrometers away from a nearest surface of said individual liver portion, said collection of liver portions being located within said chamber and said collection of liver portions being in contact with at least a portion of the fluid flowing through said chamber; said collection of liver portions being provided within a continuous liver planar organ formed by coculturing hepatocyte cells in presence of said collection of liver portions, such that said continuous liver planar organ is formed from an admixture of cells derived from said liver portions and said hepatocyte cells.
   (c) a first tube having first and second ends, said first end for coupling to the subject for receiving the fluid from the subject, said second end for coupling to said inlet; and
   (d) a second tube having first and second ends, said first end for coupling to said outlet and said second end for coupling to the subject to return the fluid to the subject after the biological modification.

12. The device according to claim 11, wherein said collection of liver portions are provided in a plurality of sheets incorporated substantially parallel in orientation within said chamber.

13. The device according to claim 12, wherein each of said sheets has a first dimension in a range of from about 30 cm to about 90 cm, a second dimension in a range of from about 30 cm to about 80 cm and a third dimension in a range of from about 300 micrometers to about 900 micrometers.

14. The device according to claim 12, wherein said plurality of sheets are incorporated substantially parallel in orientation within said chamber.

15. The device according to claim 11, further comprising a porous membrane located substantially within said chamber, said membrane effecting said contact of the fluid and said collection of liver portions.

16. The device according to claim 15, wherein said membrane permits passage therethrough of particles having a molecular weight less than from about 40,000 Da to about 250,000 Da.

17. The device according to claim 15, wherein said membrane restricts passage therethrough of white blood cells, red blood cells and immunoglobulins.

18. The device according to claim 15, wherein said plurality of sheets are characterized by being cryopreserved before being located substantially within said chamber.

19. A method of performing a biological modification of a fluid from a subject, the method comprising the step of perfusing a chamber containing a collection of liver portions with the fluid from the subject, such that said collection of liver portions performs the biological modification on the fluid, wherein each individual liver portion of said collection includes liver cells and has dimensions, such that liver cells positioned deepest within said individual liver portion are at least about 150 micrometers and not more than about 225 micrometers away from a nearest surface of said individual liver portion.

20. The method of claim 19, wherein the fluid is blood.

21. The method according to claim 19, wherein said collection of liver portions is provided within a continuous liver planar organ formed by coculturing hepatocyte cells in presence of said collection of liver portions, such that said continuous liver planar organ is formed from an admixture of cells derived from said portions and said hepatocyte cells.

22. The method according to claim 19, wherein said collection of liver portions is encapsulated by a sheet of a biocompatible polymer, said sheet being located within said chamber.

23. The method according to claim 22, wherein said sheet has a first dimension in a range of from about 30 cm to about 90 cm, a second dimension in a range of from about 30 cm to about 80 cm and a third dimension in a range of from about 300 micrometers to about 900 micrometers.

24. The method according to claim 22, wherein a plurality of said sheets are incorporated substantially parallel in orientation within said chamber.

25. The method according to claim 19, wherein said chamber includes a porous membrane located therein, said membrane effecting said contact of the fluid and said collection of liver portions.

26. The method according to claim 25, wherein said membrane permits passage therethrough of particles having a molecular weight less than from about 40,000 Da to about 250,000 Da.

27. The method according to claim 25, wherein said membrane restricts passage therethrough of white blood cell, red blood cells and immunoglobulins.

28. The method according to claim 25, wherein said sheet is characterized by being cryopreserved before being located substantially within said chamber.

29. The method according to claim 19, further comprising the step of returning the fluid to the subject.

30. The method according to claim 29, further comprising the step of returning at least one product secreted by said collection of liver portions to the subject.

31. A method of preparing a continuous liver planar organ comprising the steps of:
   (a) obtaining a collection of individual liver portions, such that each of said individual liver portions of said collection includes liver cells and has dimensions, such that cells positioned deepest within said individual portions are at least about 150 micrometers and not more than about 225 micrometers away from a nearest surface of said individual portions; and
   (b) adding a suspension of cells onto said liver portions and coculturing said suspension of cells in presence of said collection of liver portions, such that the continuous planar liver organ is formed from an admixture of cells derived from said portions and said cells.

32. A device for performing a biological modification of a fluid, the device comprising:
   (a) a chamber having an inlet for intake of the fluid and an outlet for outflow of the fluid; and
   (b) a collection of liver portions for performing the biological modification of the fluid, each individual liver portion of said collection including liver cells and having dimensions, such that liver cells positioned deepest within said individual liver portion are at least about 150 micrometers and not more than about 225 micrometers away from a nearest surface of said individual liver portion, said collection of liver portions being located within said chamber and said collection of liver portions being in contact with at least a portion of the fluid flowing through said chamber, said collection of liver portions is encapsulated by a sheet of a biocompatible polymer, said sheet being located within said chamber.

33. The device according to claim 32, wherein said collection of liver portions is provided within a continuous liver planar organ formed by coculturing hepatocyte cells in presence of said collection of liver portions, such that said continuous liver planar organ is formed from an admixture of cells derived from said liver portions and said hepatocyte cells.

34. The device according to claim 32, wherein said sheet has a first dimension in a range of from about 30 cm to about 90 cm, a second dimension in a range of from about 30 cm to about 80 cm and a third dimension in a range of from about 300 micrometers to about 900 micrometers.

35. The device according to claim 32, wherein a plurality of said sheet are incorporated substantially parallel in orientation within said chamber.

36. The device according to claim 32, further comprising a porous membrane located substantially within said chamber, said membrane effecting said contact of the fluid and said collection of liver portions.

37. The device according to claim 36, wherein said membrane permits passage therethrough of particles having a molecular weight less than from about 40,000 Da to about 250,000 Da.

38. The device according to claim 36, wherein said membrane restricts passage therethrough of white blood cells, red blood cells and immunoglobulins.

39. The device according to claim 32, further comprising a plurality of tubes for connection to a subject containing the fluid to be biologically modified, at least one of said tubes being connected to said inlet and at least a second of said tubes being connected to said outlet.

40. The device according to claims 32, wherein said collection of liver portions is characterized by being cryopreserved before being located within said chamber.

41. The device according to claim 32, wherein said sheet is characterized by being cryopreserved before being located within said chamber.

42. A device for performing a biological modification of a fluid of a subject, comprising:
    (a) a chamber having an inlet for intake of the fluid and an outlet for outflow of the fluid;
    (b) a collection of liver portions for performing the biological modification of the fluid, each individual liver portion of said collection including liver cells and having dimensions, such that liver cells positioned deepest within said individual liver portion are at least about 150 micrometers and not more than about 225 micrometers away from a nearest surface of said individual liver portion, said collection of liver portions being located within said chamber and said collection of liver portions being in contact with at least a portion of the fluid flowing through said chamber, said collection of liver portions being provided in a plurality of sheets incorporated substantially parallel in orientation within said chamber;
    (c) a first tube having first and second ends, said first end for coupling to the subject for receiving the fluid from the subject, said second end for coupling to said inlet; and
    (d) a second tube having first and second ends, said first end for coupling to said outlet and said second end for coupling to the subject to return the fluid to the subject after the biological modification.

43. The device according to claim 42, wherein said collection of liver portions is provided within a continuous liver planar organ formed by coculturing hepatocyte cells in presence of said collection of liver portions, such that said continuous liver planar organ is formed from an admixture of cells derived from said portions and said hepatocyte cells.

44. The device according to claim 42, wherein each of said sheets has a first dimension in a range of from about 30 cm to about 90 cm, a second dimension in a range of from about 30 cm to about 80 cm and a third dimension in a range of from about 300 micrometers to about 900 micrometers.

45. The device according to claims 42, wherein said plurality of sheets are incorporated substantially parallel in orientation within said chamber.

46. The device according to claim 42, further comprising a porous membrane located substantially within said chamber, said membrane effecting said contact of the fluid and said collection of liver portions.

47. The device according to claim 46, wherein said membrane permits passage therethrough of particles having a molecular weight less than from about 40,000 Da to about 250,000 Da.

48. The device according to claim 46, wherein said membrane restricts passage therethrough of white blood cells, red blood cells and immunoglobulins.

49. The device according to claim 46, wherein said plurality of sheets are characterized by being cryopreserved before being located substantially within said chamber.

50. A device for performing a biological modification of a fluid, the device comprising:
    (a) a chamber having an inlet for intake of the fluid and an outlet for outflow of the fluid;
    (b) a collection of liver portions for performing the biological modification of the fluid, each individual liver portion of said collection including liver cells and having dimensions, such that liver cells positioned deepest within said individual liver portion are at least about 150 micrometers and not more than about 225 micrometers away from a nearest surface of said individual liver portion, said collection of liver portions being located within said chamber and said collection of liver portions being in contact with at least a portion of the fluid flowing through said chamber; and
    (c) a porous membrane located substantially within said chamber, said membrane effecting said contact of the fluid and said collection of liver portions, said membrane being for restricting passage therethrough of white blood cells, red blood cells and immunoglobulins.

51. The device according to claim 50, wherein said collection of liver portions is provided within a continuous liver planar organ formed by coculturing hepatocyte cells in presence of said collection of liver portions, such that said continuous liver planar organ is formed from an admixture of cells derived from said liver portions and said hepatocyte cells.

52. The device according to claim 50, wherein said collection of liver portions is encapsulated by a sheet of a biocompatible polymer, said sheet being located within said chamber.

53. The device according to claim 52, wherein said sheet has a first dimension in a range of from about 30 cm to about 90 cm, a second dimension in a range of from about 30 cm to about 80 cm and a third dimension in a range of from about 300 micrometers to about 900 micrometers.

54. The device according to claim 52, wherein a plurality of said sheets are incorporated substantially parallel in orientation within said chamber.

55. The device according to claim 50, wherein said membrane permits passage therethrough of particles having a molecular weight less than from about 40,000 Da to about 250,000 Da.

56. The device according to claim 50, further comprising a plurality of tubes for connection to a subject containing the fluid to be biologically modified, at least one of said tubes being connected to said inlet and at least a second of said tubes being connected to said outlet.

57. The device according to claim 50, wherein said collection of liver portions is characterized by being cryopreserved before being located within said chamber.

58. The device according to claim 52, wherein said sheet is characterized by being cryopreserved before being located within said chamber.

59. A device for performing a biological modification of a fluid of a subject, comprising:
   (a) a chamber having an inlet for intake of the fluid and an outlet for outflow of the fluid;
   (b) a collection of liver portions for performing the biological modification of the fluid, each individual liver portion of said collection including liver cells and having dimensions, such that liver cells positioned deepest within said individual liver portion are at least about 150 micrometers and not more than about 225 micrometers away from a nearest surface of said individual liver portion, said collection of liver portions being located within said chamber and said collection of liver portions being in contact with at least a portion of the fluid flowing through said chamber;
   (c) a porous membrane located substantially within said chamber, said membrane effecting said contact of the fluid and said collection of liver portions, said membrane being for restricting passage therethrough of white blood cells, red blood cells and immunoglobulins;
   (d) a first tube having first and second ends, said first end for coupling to the subject for receiving the fluid from the subject, said second end for coupling to said inlet; and
   (e) a second tube having first and second ends, said first end for coupling to said outlet and said second end for coupling to the subject to return the fluid to the subject after the biological modification.

60. The device according to claim 59, wherein said collection of liver portions is provided within a continuous liver planar organ formed by coculturing hepatocyte cells in presence of said collection of liver portions, such that said continuous liver planar organ is formed from an admixture of cells derived from said portions and said hepatocyte cells.

61. The device according to claim 59, wherein said collection of liver portions are provided in a plurality of sheets incorporated substantially parallel in orientation within said chamber.

62. The device according to claim 61, wherein each of said sheets has a first dimension in a range of from about 30 cm to about 90 cm, a second dimension in a range of from about 30 cm to about 80 cm and a third dimension in a range of from about 300 micrometers to about 900 micrometers.

63. The device according to claim 61, wherein said plurality of sheets are incorporated substantially parallel in orientation within said chamber.

64. The device according to claim 59, wherein said membrane permits passage therethrough of particles having a molecular weight less than from about 40,000 Da to about 250,000 Da.

65. The device according to claim 63, wherein said plurality of sheets are characterized by being cryopreserved before being located substantially within said chamber.

* * * * *